(12) United States Patent
Hashimoto

(10) Patent No.: US 6,429,212 B1
(45) Date of Patent: Aug. 6, 2002

(54) MEDICINAL COMPOSITION

(75) Inventor: Yuichi Hashimoto, Tokyo (JP)

(73) Assignee: Ishihara Sangyo Kaisha Ltd., Osaka (JP)

(*) Notice: Subject to any disclaimer, the term of this patent is extended or adjusted under 35 U.S.C. 154(b) by 0 days.

(21) Appl. No.: 09/147,687

(22) PCT Filed: Aug. 14, 1997

(86) PCT No.: PCT/JP97/02832

§ 371 (c)(1),
(2), (4) Date: Feb. 16, 1999

(87) PCT Pub. No.: WO98/07421

PCT Pub. Date: Feb. 26, 1998

(30) Foreign Application Priority Data

| Aug. 16, 1996 | (JP) | 8-234672 |
| Jun. 11, 1997 | (JP) | 9-171122 |
| Jun. 11, 1997 | (JP) | 9-171123 |
| Jun. 11, 1997 | (JP) | 9-171124 |

(51) Int. Cl.[7] ............... A61K 31/47; A61K 31/40; C07D 221/02; C07D 209/48; C07D 487/14
(52) U.S. Cl. .......... 514/309; 514/417; 546/183; 546/141; 548/473; 548/480; 548/422
(58) Field of Search ............... 514/309, 417; 546/183, 141; 548/473, 480, 422

(56) References Cited

U.S. PATENT DOCUMENTS 5,643,943 A * 7/1997 Gamache et al.

FOREIGN PATENT DOCUMENTS

| JP | 50121432 | * | 9/1975 |
| JP | 55-72151 | * | 5/1980 |
| JP | 57-32218 | * | 2/1982 |
| JP | 60-130561 | * | 7/1985 |
| JP | 62022760 | * | 1/1987 |
| JP | 2-145567 | * | 6/1990 |
| JP | 4-175303 | * | 6/1992 |
| WO | WO 92/8704 | * | 5/1992 |
| WO | WO 93/22291 | * | 11/1993 |
| WO | WO 96/11209 | * | 4/1996 |
| WO | WO 96/20926 | * | 7/1996 |
| WO | WO 97/23457 | * | 7/1997 |

OTHER PUBLICATIONS

Moreira Et Al, "Comparison of Pentoxifykkine, Thalidomide and Prednisone in the Treatment of Encl." Int. J. Leprosy 66, 61, 1998.

Miyachi Et Al, "Inducer–Specific Bidirectional Regulation by Thalidomide and Phenylphthalimides of Tumor Necrosis Factor–α Production", Biochem. Biophys. Res. Commun, 224, 426–430, 1996.

* cited by examiner

Primary Examiner—T. A. Solola
Assistant Examiner—Joseph Murray
(74) Attorney, Agent, or Firm—Oblon, Spivak, McClelland, Maier & Neustadt, P.C.

(57) ABSTRACT

It is to provide a cyclic imide derivative which is useful as an active ingredient of a pharmaceutical composition. A pharmaceutical composition which comprises, a cyclic imide derivative represented by the general formula (I):

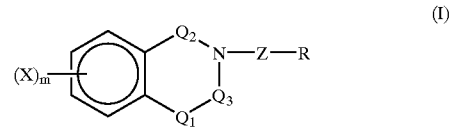

wherein $Q_1$ is a single bond, $-CH_2-$, $-O-$, $-S-$ or $-NH-$, each of $Q_2$ and $Q_3$ is $-C(O)-$, $-C(S)-$ or $-CH_2-$, provided that at least one of $Q_2$ and $Q_3$ is $-C(O)-$ or $-C(S)-$, Z is a single bond or a lower alkanediyl group, R is an aryl group which may be substituted or a cycloalkyl group which may be substituted, X is a nitro group, an amino group which may be acylated, a cyano group, a trifluoromethyl group, a hydroxyl group, a halogen atom, an alkyl group, an alkoxy group or an alkylthio group, m is an integer of from 0 to 4, and when m is 2 or above, X may be the same or different, or its salt.

10 Claims, No Drawings

MEDICINAL COMPOSITION

This application is 371 of PCT/JP97/02832 filed Aug. 14, 1997.

TECHNICAL FIELD

The present invention relates to a pharmaceutical composition which comprises a cyclic imide derivative or its salt. The cyclic imide derivative or its salt includes the isoindole derivative or its salt, a certain N-phenylimide compound or its salt, a certain phthalimide derivative or its salt, and an N-phenylphthalimide derivative or its salt. Particularly, the present invention relates to an aminopeptidase N inhibitor or an angiogenesis inhibitor, which comprises, as an active ingredient, the cyclic imide derivative or its salt.

The present invention further relates to a novel isoindole derivative or its salt, a method for producing it, and a pharmaceutical composition comprising it. It also relates to a pharmaceutical which modulates production of tumor necrosis factor (TNF-α) and which comprises, as an active ingredient, a novel isoindole derivative or its salt.

BACKGROUND ART

JP-A-50-121432 discloses phthalimide derivatives as active ingredients for agricultural and horticultural fungicides, and JP-A-62-22760 discloses isoindoline derivatives as active ingredients for agricultural and horticultural fungicides. However, they are respectively different in their chemical structures from the cyclic imide derivatives of the present invention.

Further, in the field of pharmaceuticals, the cyclic imide derivatives of the present invention differ in the chemical structures from N-alkylphthalimides disclosed in CHEMICAL & PHARMACEUTICAL BULLETIN vol. 43, 1, 177–179, 1995, and from benzylphthalimides and phenethylphthalimides disclosed in BIOLOGICAL PHARMACEUTICAL BULLETIN vol. 18, 9, 1228–1233, 1995.

A pharmaceutical which modulates (enhances or suppresses) production of tumor necrosis factor (TNF-α) which is considered to be one of factors which cause various diseases, is useful also as a biological response modulator. It is expected to be used widely, as an immunostimulant or an immunosuppressant, and development of it as a pharmaceutical is desired.

Further, aminopeptidase N (APN) is distributed mainly in epithelial cells of kidney and small intestine, monocytes and granulocytes, cancer cells and on cell surface membrane of placenta, liver and pancreas, and its various physiological functions such as digestion and absorption of amino acids, biosyntheses and degradation of bioactive substances such as peptide hormones, growth factors and autacoid and degradation of extracellular matrix, have been studied. And a pharmaceutical which inhibits the activity of APN is expected as a preventive drug or a therapeutic drug for cancer, cancer metastasis, inflammatory diseases, autoimmune diseases and allergic diseases, and development of a pharmaceutical drug which is an aminopeptidase N inhibitor is desired.

Excessive activation of angiogenesis is known to relate to onset or progression steps of various diseases, and development of a pharmaceutical which is an angiogenesis inhibitor which is useful as a preventive drug or a therapeutic drug of such diseases is desired.

Further, it is meaningful to find out an excellent pharmaceutical composition with respect to a certain novel and characteristic isoindole derivative or its salt.

DISCLOSURE OF THE INVENTION

In order to find out an excellent pharmaceutical a composition with respect to a certain isoindole derivative or its salt, the present inventors have paid attention to modulate production of tumor necrosis factor (TNF-α) which is considered to be one of factors which cause various diseases. Further, they have found that by using an optically active substance of the isoindole derivative or its salt, the control of TNF-α production can be divided into enhancing effect and suppressive effect, whereby a compound which has only one of these effects can be obtained, and as a result, they have accomplished the present invention.

Further, they have found that a cyclic imide derivative having a certain chemical structure or its salt has amino peptidase N inhibitory effect or anti-angiogenetic effect, and have accomplished the present invention.

Namely, the present invention relates to:

(1) An aminopeptidase N inhibitor which comprises a cyclic imide derivative represented by the general formula (I):

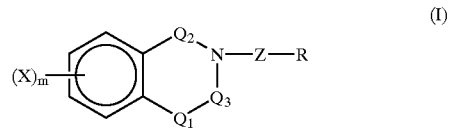

wherein $Q_1$ is a single bond, —$CH_2$—, —O—, —S— or —NH—, each of $Q_2$ and $Q_3$ which are independent of each other, is —C(O)—, —C(S)— or —$CH_2$—, provided that at least one of $Q_2$ and $Q_3$ is —C(O)— or —C(S)—, Z is a single bond or a lower alkanediyl group, R is an aryl group which may be substituted or a cycloalkyl group which may be substituted, X is a nitro group, an amino group which may be acylated, a cyano group, a trifluoromethyl group, a hydroxyl group, a halogen atom, an alkyl group, an alkoxy group or an alkylthio group, m is an integer of from 0 to 4, and when m is 2 or above, X may be the same or different, or its salt, and a pharmaceutically acceptable carrier;

(2) The aminopeptidase N inhibitor according to (1), wherein in the cyclic imide derivative, $Q_1$ is a single bond or —$CH_2$—, and Z is a single bond;

(3) The aminopeptidase N inhibitor according to (1), wherein in the cyclic imide derivative, $Q_1$ is a single bond or —$CH_2$—, Z is a single bond, and R is a phenyl group which may be substituted;

(4) The aminopeptidase N inhibitor according to (1), wherein in the cyclic imide derivative, $Q_1$ is —$CH_2$—, Z is a single bond, and R is a phenyl group which may be substituted;

(5) An angiogenesis inhibitor which comprises a cyclic imide derivative represented by the general formula (I):

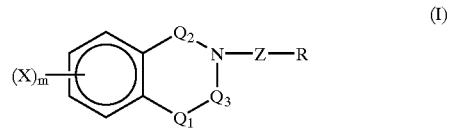

wherein $Q_1$ is a single bond, —$CH_2$—, —O—, —S— or —NH—, each of $Q_2$ and $Q_3$ which are independent of each other, is —C(O)—, —C(S)—, or —$CH_2$—, provided that at least one of $Q_2$ and $Q_3$ is —C(O)— or —C(S)—, Z is a single bond or a lower alkanediyl group, R is an aryl group which may be substituted or a cycloalkyl group which may be substituted, X is a nitro group, an amino group which may be acylated, a cyano group, a trifluoromethyl group, a hydroxyl group, a halogen atom, an alkyl group, an alkoxy group or an alkylthio group, m is an integer of from 0 to 4, when m is 2 or above, X may be the same or different, and provided that when Z is a single bond, R is an aryl group which may be substituted, or its salt, and a pharmaceutically acceptable carrier;

(6) The angiogenesis inhibitor according to (5), wherein $Q_1$ in the cyclic imide derivative is a single bond or —$CH_2$—;

(7) The angiogenesis inhibitor according to (5), wherein in the cyclic imide derivative, $Q_1$ is a single bond or —$CH_2$—, and R is a phenyl group which may be substituted, a naphthyl group which may be substituted or a cyclohexyl group which may be substituted;

(8) The angiogenesis inhibitor according to (5), wherein in the cyclic imide derivative, $Q_1$ is a single bond or —$CH_2$—, Z is a single bond or a 1,1-ethanediyl group, R is a phenyl group which may be substituted, a inaphthyl group which may be substituted or a cyclohexyl group which may be substituted;

(9) The angiogenesis inhibitor according to (5), wherein in the cyclic imide derivative, $Q_1$ is a single bond or —$CH_2$—, Z is a single bond or a 1,1-ethanediyl group, R is a phenyl group which may be substituted, a naphthyl group which may be substituted or a cyclohexyl group which may be substituted, X is a fluorine atom and m is 4;

(10) A cyclic imide derivative represented by the general formula (I'):

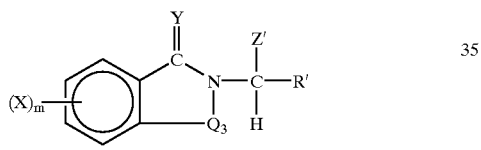

(I')

wherein Z' is an alkyl group, R' is a phenyl group which may be substituted, a naphthyl group which may be substituted or a cyclohexyl group which may be substituted, X is a nitro group, an amino group which may be acylated, a cyano group, a trifluoromethyl group, a hydroxyl group, a halogen atom, an alkyl group, an alkoxy group or an alkylthio group, m is an integer of from 0 to 4, when m is 2 or above, X may be the same or different, Y is an oxygen atom or a sulfur atom, and $Q_3$ is —C(O)—, —C(S)— or —$CH_2$—, or its salt;

(11) The cyclic imide derivative according to (10), wherein the compound of the formula (I') is an optically active substance of S-form or R-form, or its salt;

(12) The cyclic imide derivative according to (10) or (11), wherein Z' is a methyl group, or its salt;

(13) The cyclic imide derivative according to (10) or (11), wherein Z' is a methyl group, X is a fluorine atom and m is 4, or its salt;

(14) A pharmaceutical composition, which comprises the cyclic imide derivative as defined in (10), or its salt and a pharmaceutically acceptable carrier;

(15) A TNF-α production modulator which comprises the cyclic imide derivative as defined in (10), or its salt and a pharmaceutically acceptable carrier;

(16) The cyclic imide derivative according to (10), which is an isoindole derivative represented by the general formula (I"):

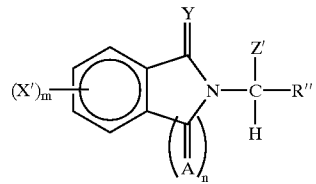

(I")

wherein Z' is an alkyl group, R" is a phenyl group which may be substituted, a naphthyl group which may be substituted or a cyclohexyl group which may be substituted, the substituent is a nitro group, an amino group, a lower acylamino group, an alkoxy group, an alkylthio group or an alkyl group, X' is a nitro group, an amino group, a cyano group, a trifluoromethyl group, a hydroxyl group, a halogen atom or an alkyl group, each of Y and A which are independent of each other, is an oxygen atom or a sulfur atom, m is an integer of from 0 to 4, when m is 2 or above, X' may be the same or different, and n is 0 or 1, or its salt;

(17) The cyclic imide derivative according to (16), wherein Z' is a methyl group, R" is a phenyl group, a naphthyl group or a cyclohexyl group, X' is a fluorine atom, each of Y and A is an oxygen atom, m is 0 or 4, and n is 1, or its salt;

(18) The pharmaceutical composition according to (14), which comprises, as an active ingredient, an isoindole derivative represented by the general formula (I"):

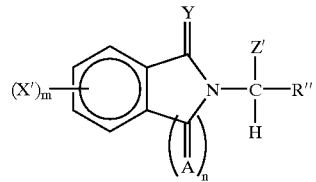

(I")

wherein Z' is an alkyl group, R" is a phenyl group which may be substituted, a naphthyl group which may be substituted or a cyclohexyl group which may be substituted, provided that the substituent is a nitro group, an amino group, a lower acyl amino group, an alkoxy group, an alkylthio group or an alkyl group, X' is a nitro group, an amino group, a cyano group, a trifluoromethyl group, a hydroxyl group, a halogen atom or an alkyl group, each of Y and A which are independent of each other, is an oxygen atom or a sulfur atom, m is an integer of from 0 to 4, when m is 2 or above, X' may be the same or different, and n is 0 or 1, or its salt;

(19) A TNF-α production modulator which comprises, as an active ingredient, the isoindole derivative or its salt, as the pharmaceutical composition as defined in (18);

(20) The TNF-α production modulator according to (19), wherein the isoindole derivative or its salt is an optically active substance of S-form or R-form;

(21) The TNF-α production suppressant according to (20), wherein the isoindole derivative or its salt is an optically active substance of R-form;

(22) The TNF-α production suppressant according to (21), wherein the isoindole derivative or its salt is an optically active substance of R-form, wherein Z' is a methyl group, R" is a phenyl group, a naphthyl group or a cyclohexyl group, X' is a fluorine atom, each of Y and A is an oxygen atom, m is 0 or 4, and n is 1;

(23) A method for producing a cyclic imide derivative represented by the general formula (I'-1):

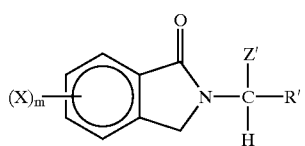
(I'-1)

wherein Z' is an alkyl group, R' is a phenyl group which may be substituted, a naphthyl group which may be substituted or a cyclohexyl group which may be substituted, X is a nitro group, an amino group which may be acylated, a cyano group, a trifluoromethyl group, a hydroxyl group, a halogen atom, an alkyl group, an alkoxy group or an alkylthio group, m is an integer of from 0 to 4, and when m is 2 or above, X may be the same or different, or its salt; which comprises reacting a phthalaldehyde corresponding to the cyclic imide derivative represented by the general formula (I'-1), with a compound of the general formula (III):

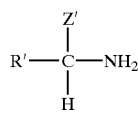
(III)

wherein Z' and R' are as defined above; and conducting a salt-forming reaction, as the case requires;

(24) A method for producing a cyclic imide derivative represented by the general formula (I'-2):

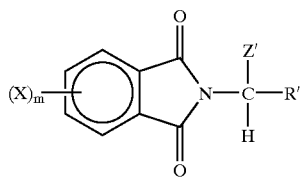
(I'-2)

wherein Z' is an alkyl group, R' is a phenyl group which may be substituted, a naphthyl group which may be substituted or a cyclohexyl group which may be substituted, X is a nitro group, an amino group which may be acylated, a cyano group, a trifluoromethyl group, a hydroxyl group, a halogen atom, an alkyl group, an alkoxy group or an alkylthio group, m is an integer of from 0 to 4, and when m is 2 or above, X may be the same or different, or its salt; which comprises reacting a compound of the general formula (II):

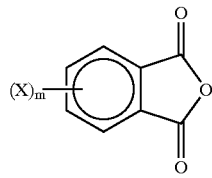
(II)

wherein X and m are as defined above, with a compound of the general formula (III):

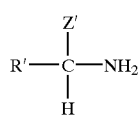
(III)

wherein Z' and R' are as defined above; and conducting a salt-forming reaction, as the case requires; and

(25) A method for producing a cyclic imide derivative represented by the general formula (I'-3):

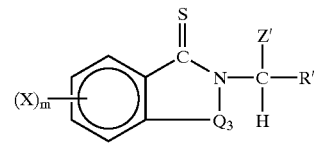
(I'-3)

wherein Z' is an alkyl group, R' is a phenyl group which may be substituted, a naphthyl group which may be substituted or a cyclohexyl group which may be substituted, X is a nitro group, an amino group which may be acylated, a cyano group, a trifluoromethyl group, a hydroxyl group, a halogen atom, an alkyl group, an alkoxy group or an alkylthio group, m is an integer of from 0 to 4, when m is 2 or above, X may be the same or different, and $Q_3$ is —C(O)—, —C(S)— or —CH$_2$—, or its salt; which comprises reacting a compound of the general formula (I'-4):

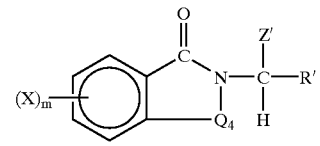
(I'-4)

wherein Z', R', X and m are as defined above, and $Q_4$ is —C(O)— or —CH$_2$—, with di-phosphorus pentasulfide; and conducting a salt-forming reaction as the case requires.

In another mode, the present invention provides:

(26) An aminopeptidase N inhibitor according to (1), which comprises an N-phenylimide derivative represented by the general formula (I'''-1) or (I'''-2):

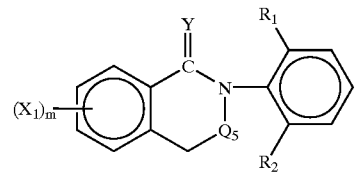
(I'''-1)

or

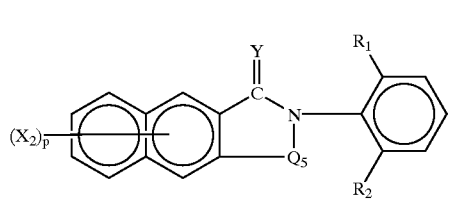
(I'''-2)

wherein each of $R_1$ and $R_2$ is a hydrogen atom, a lower alkyl group, a lower alkoxy group or a lower alkylthio group, Y is an oxygen atom or a sulfur atom, each of $X_1$ and $X_2$ is a halogen atom, a nitro group, a cyano group, a trifluoromethyl group, a hydroxyl group, an amino group which may be acylated, an alkyl group, an alkoxy group or an alkylthio group, m is 0 or an integer of from 1 to 4, when m is 2 or above, $X_1$ may be the same or different, p is 0 or an integer of from 1 to 6, when p is 2 or above, $X_2$ may be the same or different, and $Q_5$ is —C(O)— or —CH$_2$—, or its salt and a pharmaceutically acceptable carrier;

(27) The aminopeptidase N inhibitor according to (26), wherein both $R_1$ and $R_2$ are isopropyl groups, Y is an oxygen atom, m or p is 0, and $Q_5$ is —C(O)—;

(28) The angiogenesis inhibitor according to (5), which comprises an N-phenylimide compound represented by the general formula (I'''-1) or (I'''-2):

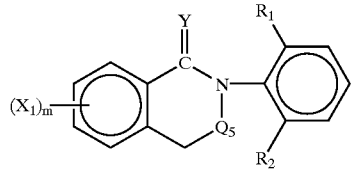

(I'''-1)

or

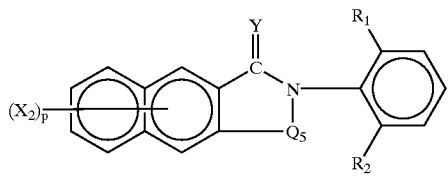

(I'''-2)

wherein each of $R_1$ and $R_2$ is a hydrogen atom, a lower alkyl group, a lower alkoxy group or a lower alkylthio group, Y is an oxygen atom or a sulfur atom, each of $X_1$ and $X_2$ is a halogen atom, a nitro group, a cyano group, a trifluoromethyl group, a hydroxyl group, an amino group which may be acylated, an alkyl group, an alkoxy group or an alkylthio group, m is 0 or an integer of from 1 to 4, when m is 2 or above, $X_1$ may be the same or different, p is 0 or an integer of from 1 to 6, when p is 2 or above, $X_2$ may be the same or different, and $Q_5$ is —C(O)— or —CH$_2$—, or its salt and a pharmaceutically acceptable carrier;

(29) The angiogenesis inhibitor according to (28), wherein both $R_1$ and $R_2$ are isopropyl groups, Y is an oxygen atom, m or p is 0, and $Q_5$ is —C(O)—;

(30) The aminopeptidase N inhibitor according to (1), which comprises a phthalimide derivative represented by the general formula (I''''):

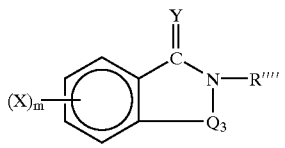

(I'''')

wherein R'''' is an adamantyl group, a 2,6-diisopropylphenyl group or a 2-lower-alkylthiophenyl group, X is a nitro group, an amino group which may be acylated, a cyano group, a trifluoromethyl group, a hydroxyl group, a halogen atom, an alkyl group, an alkoxy group or an alkylthio group, Y is an oxygen atom or a sulfur atom, $Q_3$ is —C(O)—, —C(S)— or —CH$_2$—, m is an integer of from 0 to 4, and when m is 2 or above, X may be the same or different, or its salt and a pharmaceutically acceptable carrier;

(31) The angiogenesis inhibitor according to (5), which comprises a phthalimide derivative represented by the general formula (I''''):

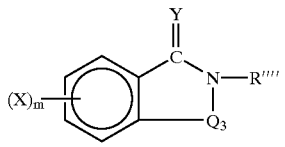

(I'''')

wherein R'''' is an adamantyl group, a 2,6-diisopropylphenyl group or a 2-lower-alkylthiophenyl group, X is a nitro group, an amino group which may be acylated, a cyano group, a trifluoromethyl group, a hydroxyl group, a halogen atom, an alkyl group, an alkoxy group or an alkylthio group, Y is an oxygen atom or a sulfur atom, $Q_3$ is —C(O)—, —C(S)— or —CH$_2$—, m is an integer of from 0 to 4, and when m is 2 or above, X may be the same or different, or its salt and a pharmaceutically acceptable carrier;

(32) The angiogenesis inhibitor according to (5), which comprises at least one N-phenylphthalimide derivative selected from the group consisting of N-phenylphthalimide, N-phenylthiophthalimide, N-(2,6-diisopropylphenyl)-phthalimide, N-(2,6-diisopropylphenyl)-4,5,6,7-tetrafluoro-phthalimide, N-(2,6-diisopropylphenyl)-4-nitrophthalimide and N-(2,6-diisopropylphenyl)-5-nitrophthalimide, or its salt and a pharmaceutically acceptable carrier;

(33) The pharmaceutical composition according to (18), which has an enhancing effect of production of tumor necrosis factor (TNF-α);

(34) The pharmaceutical composition according to (18), which has a suppressive effect of production of tumor necrosis factor (TNF-α);

(35) The pharmaceutical composition according to (18), which has a favorable influence upon at least one bioactivity selected from the group consisting of cytotoxicity against tumor cells, activation of T cells, activation of anti-tumor macrophages, activation of neutrophils, induction of interferon-β$_2$ by fibroblasts, and stimulation of immuno systems;

(36) The pharmaceutical composition according to (18), which suppresses at least one bioactivity selected from the group consisting of enhancement of cancer metastasis and angiogenesis, induction of endotoxin shock, induction of inflammation of organs and tissues, inhibition of lipoprotein lipase of adipocytes, and induction of replication of human immunodeficiency viruses;

(37) The pharmaceutical composition according to (18), which has inflammation suppressive effect or immune modulation effect;

(38) The pharmaceutical composition according to (18), which is a preventive drug or a therapeutic drug for autoimmune diseases such as rheumatic fever or rheumatoid arthritis, erythema nodosum leprosum, Behchet's disease, lupus erythematosus or aphthous ulcer;

(39) The pharmaceutical composition according to (18), which is a preventive drug or a therapeutic drug for a cachexia in cancer or infectious diseases, septic shock, adult respiratory distress syndrome, osteoarthritis, multiple sclerosis, inflammatory enteropathy, multiple organ failure, malaria, meningitidis, hepatitis, diabetes or acquired immunodeficiency syndrome;

(40) The pharmaceutical composition according to (18), which suppresses side effects caused by TNF-α;

(41) A controlling agent of biological response which comprises, as an active ingredient, the isoindole derivative or its salt, as the pharmaceutical composition as defined in (18);

(42) A biological response modulator which comprises, as an active ingredient, the isoindole derivative or its salt, as the pharmaceutical composition as defined (18);

(43) An immunostimulant which comprises, as an active ingredient, the isoindole derivative or its salt, as the pharmaceutical composition as defined in (18);

(44) The immunostimulant according to (43), which is a therapeutic drug for cancer;

(45) An immunosuppressant which comprises, as an active ingredient, the isoindole derivative or its salt, as the pharmaceutical composition as defined in (18);

(46) The immunosuppressant according to (45), which is a therapeutic drug for transplant graft rejection, graft versus host diseases or immune diseases;

(47) The angiogenesis inhibitor according to (5), which is a preventive drug or a therapeutic drug for at least one disease selected from the group consisting of cancer; cancer metastasis; benign tumors including angioma, auditory neuroma, neurofibroma, trachoma, purulent granuloma and granulation; chronic inflammatory diseases including rheumatoid arthritis; psoriasis; eye diseases relating to angiogenesis including diabetic retinopathy, retinopathy of prematurity, macular degeneration, glaucoma, retrolental fibroplasia and central retinal vein atresia; angiogenesis resulting from corneal transplantation; hypertrophic scar; atherosclerosis; scleredema and nephropathy;

(48) The aminopeptidase N inhibitor according to (1), which has a favorable influence upon at least one bioactivity selected from the group consisting of digestion and absorption of amino acids; biosyntheses and degradation of bioactive substances including peptide hormones, growth factors and autacoids; and degradation of extracellular matrix;

(49) The aminopeptidase N inhibitor according to (1), which has immune function modulation effect;

(50) The aminopeptidase N inhibitor according to (1), which suppresses metastasis of cancer cells;

(51) The aminopeptidase N inhibitor according to (1), which is a preventive drug or a therapeutic drug for at least one disease selected from the group consisting of cancer, cancer metastasis, inflammatory diseases, autoimmune diseases and allergic diseases;

(52) The aminopeptidase N inhibitor according to (1), wherein the substituent for the aryl group which may be substituted or the cycloalkyl group which may be substituted in the definition of R, is selected from the group consisting of a nitro group, an amino group which may be acylated, a cyano group, a trifluoromethyl group, a hydroxyl group, a halogen atom, an alkyl group, an alkoxy group and an alkylthio group;

(53) The angiogenesis inhibitor according to (5), wherein the substituent for the aryl group which may be substituted or the cycloalkyl group which may be substituted in the definition of R, is selected from the group consisting of a nitro group, an amino group which may be acylated, a cyano group, a trifluoromethyl group, a hydroxyl group, a halogen atom, an alkyl group, an alkoxy group and an alkylthio group;

(54) The cyclic imide derivative according to (10), wherein the substituent for the phenyl group which may be substituted, the naphthyl group which may be substituted or the cyclohexyl group which may be substituted in the definition of R', is selected from the group consisting of a nitro group, an amino group which may be acylated, a cyano group, a trifluoromethyl group, a hydroxyl group, a halogen atom, an alkyl group, an alkoxy group and an alkylthio group, or its salt;

(55) The aminopeptidase N inhibitor according to (30), which comprises the phthalimide derivative represented by the general formula (I'''') of (30), except the compound wherein (1) R'''' is a 2,6-diisopropylphenyl group, Y is an oxygen atom, $Q_3$ is —C(O)— and m is 0, (2) R'''' is a 2,6-diisopropylphenyl group, X is a halogen atom, Y is an oxygen atom, $Q_3$ is —C(O)— and m is 4, (3) R'''' is a 2,6-diisopropylphenyl group, X is a nitro group, an amino group or a hydroxyl group, Y is an oxygen atom, $Q_3$ is —C(O)— and m is 1, and (4) R'''' is an adamantyl group, Y is an oxygen atom, $Q_3$ is —C(O)— and m is 0, or its salt; and

(56) The angiogenesis inhibitor according to (31), which comprises the phthalimide derivative represented by the general formula (I'''') of (31), except the compound wherein (1) R'''' is a 2,6-diisopropylphenyl group, Y is an oxygen atom, $Q_3$ is —C(O)— and m is 0, (2) R'''' is a 2,6-diisopropylphenyl group, X is a halogen atom, Y is an oxygen atom, $Q_3$ is —C(O)— and m is 4, (3) R'''' is a 2,6-diisopropylphenyl group, X is a nitro group, an amino group or a hydroxyl group, Y is an oxygen atom, $Q_3$ is —C(O)— and m is 1, and (4) R'''' is an adamantyl group, Y is an oxygen atom, $Q_3$ is —C(O)— and m is 0, or its salt.

In one of the preferred modes, the present invention provides a cyclic imide derivative represented by the general formula (I'):

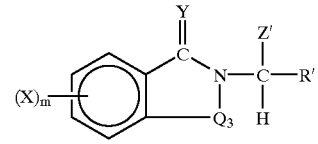

(I')

wherein Z' is an alkyl group, R' is a phenyl group which may be substituted, a naphthyl group which may be substituted or a cyclohexyl group which may be substituted, X is a nitro group, an amino group which may be acylated, a cyano group, a trifluoromethyl group, a hydroxyl group, a halogen atom, an alkyl group, an alkoxy group or an alkylthio group, m is an integer of from 0 to 4, when m is 2 or above, X may be the same or different, Y is an oxygen atom or a sulfur atom, and $Q_3$ is —C(O)—, —C(S)— or —CH$_2$—, or its salt, a method for producing it and a pharmaceutical composition comprising it.

Particularly, in one of the more preferred modes, the present invention relates to an isoindole derivative represented by the general formula (I"):

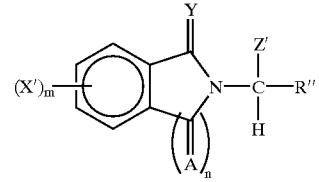

(I")

wherein Z' is an alkyl group, R" is a phenyl group which may be substituted, a naphthyl group which may be substituted or a cyclohexyl group which may be substituted, provided that the substituent is a nitro group, an amino group, a lower acylamino group, an alkoxy group, an alkylthio group or an alkyl group, X' is a nitro group, an amino group, a cyano group, a trifluoromethyl group, a hydroxyl group, a halogen atom or an alkyl group, each of Y and A which may be the same or different, is an oxygen atom or a sulfur atom, m is an integer of from 0 to 4, when m is 2 or above, X may be the same or different, and n is 0 or 1, or its salt, a method for producing it and a pharmaceutical composition comprising it.

BEST MODE FOR CARRYING OUT THE INVENTION

The present invention provides a pharmaceutical composition having aminopeptidase N inhibitory effect, which comprises, as an active ingredient, a cyclic imide derivative represented by the general formula (I) or its salt (a pharmaceutically acceptable salt); a pharmaceutical composition having angiogenesis inhibitory effect, which comprises, as an active ingredient, a cyclic imide derivative represented by the general formula (I) or its salt (a pharmaceutically acceptable salt); and further, a pharmaceutical composition, which comprises a novel cyclic imide derivative represented by the general formula (I') or its salt (a pharmaceutically acceptable salt), which, however, is included in the cyclic imide derivative represented by the general formula (I) or its salt. Further, the present invention provides a cyclic imide derivative represented by the general formula (I') or its salt, a method for producing it, and a pharmaceutical composition having tumor necrosis factor production modulating effect, which comprises, as an active ingredient, the cyclic imide derivative or its salt.

In the above-mentioned general formulae (I), (I') and (I''''), and the following general formula (I''''), the halogen atom for X may be a fluorine atom, a chlorine atom, a bromine atom or an iodine atom. As the alkyl group for X, a lower alkyl group, which is linear or branched, and has a carbon number of from 1 to 6, preferably from 1 to 4, may be mentioned, such as a methyl group, an ethyl group, a propyl group, an isopropyl group, a butyl group, a tert-butyl group, a pentyl group or a hexyl group. As the alkoxy group for X, a lower alkoxy group, which is linear or branched, and has a carbon number of from 1 to 6, preferably from 1 to 4, may be mentioned, such as a methoxy group, an ethoxy group, a propoxy group, an isopropoxy group, a butoxy group, a tert-butoxy group, a pentyloxy group or a hexyloxy group. As the alkylthio group, a lower alkylthio group, which is linear or branched, and has a carbon number of from 1 to 6, preferably from 1 to 4, may be mentioned, such as a methylthio group, an ethylthio group a propylthio group, an isopropylthio group, a butylthio group, a tert-butylthio group, a pentylthio group or a hexylthio group. The amino group for X may be substituted by an acyl group. As the acyl group, one having an alkyl group residue may be mentioned, and the alkyl group portion may be as mentioned above. The alkyl group portion in the above group may be substituted by the above-mentioned halogen atom.

In the general formula (I'''-1) or (I'''-2), the halogen atom, the alkyl group, the alkoxy group or the alkylthio group for $X_1$ or $X_2$, is as defined above for X. The amino group which may be acylated for $X_1$ or $X_2$ is as defined for X. As the halogen atom for $X_1$ or $X_2$, fluorine is preferred.

In the general formula (I), as the lower alkanediyl group for Z, a linear or branched one which has a carbon number of from 1 to 6, preferably from 1 to 4, may be mentioned, such as a methylene group, an ethylene group, a propylene group, a —CH(CH$_3$)— group, a —C(CH$_3$)$_2$— group, a —CH(CH$_3$)—CH$_2$— group, a —C(CH$_3$)$_2$CH$_2$— group, a —CH(CH$_3$)—CH(CH$_3$)— group or a —C(CH$_3$)$_2$—CH$_2$—CH$_2$— group. In the general formula (I'), as the alkyl group for Z', the alkyl group as defined above for X may be mentioned.

In the general formula (I) or (I'), as the aryl portion of the aryl group which may be substituted in the definition of R or R', monocyclic or bicyclic one, or heterocyclic one which has one or more of hetero atoms including a nitrogen atom, a sulfur atom, and an oxygen atom, such as a phenyl group, a naphthyl group, a pyridyl group, a thenyl group, a furanyl group, a pyrimidyl group, an oxazole group or an imidazole group. The substituent for the aryl group which may be substituted, may be the same as mentioned above for X. It is preferably an alkyl group, particularly a lower alkyl group, which is linear or branched, and has a carbon number of from 1 to 6, preferably from 1 to 4, such as a methyl group, an ethyl group, a propyl group, an isopropyl group, a butyl group, a tert-butyl group, a pentyl group or a hexyl group. As the more preferred substituent, a nitro group, an amino group which may be acylated such as an amino group, an alkanoylamino group, preferably an alkanoylamino group, which is linear or branched, and has a carbon number of from 1 to 6, preferably from 1 to 4, an alkylthio group, preferably an alkylthio group which is linear or branched, and has a carbon number of from 1 to 6, preferably from 1 to 4, may be mentioned. As the cycloalkyl portion of the cycloalkyl group which may be substituted in the definition of R or R', monocyclic one, bicyclic one or tricyclic one, such as a cyclopentyl group, a cyclohexyl group, a cycloheptyl group, a bicyclohexyl group or an adamantyl group may be mentioned. The substituent for the cycloalkyl group which may be substituted, may be the same as mentioned above for X. It is preferably an alkyl group, particularly a lower alkyl group which is linear or branched, and has a carbon number of from 1 to 6, preferably from 1 to 4, such as a methyl group, an ethyl group, a propyl group, an isopropyl group, a butyl group, a tert-butyl group, a pentyl group or a hexyl group. In the general formula (I'''-1) or (I'''-2), the lower alkyl group, the lower alkoxy group or the lower alkylthio group for $R_1$ or $R_2$ is as defined above for X.

In the general formula (I), (I'), (I''), (I'''-1) and (I''''), when m is 2 or above, X may be the same or different, X' and $X_1$ may also be the same or different. Further, in the general formula (I'''-2), when p is 2 or above, $X_2$ may be the same or different. In the general formula (I''), the substituent for the phenyl group which may be substituted, the naphthyl group which may be substituted or the hexyl group which may be substituted in the definition of R'', is as defined above for R and R'. The lower acylamino group may, for example, be a linear or branched lower alkanoylamino group which has a carbon number of from 1 to 6, preferably from 1 to 4.

Among the cyclic imide derivatives represented by the general formula (I), a compound wherein X is an amino group or a hydroxyl group (and/or a compound wherein R has an amino group or a hydroxyl group as a substituent) may form a salt. The salt may be any salt so long as it is pharmaceutically acceptable. For example, it includes an inorganic acid salt such as hydrochloride, sulfate and nitrate; an organic acid salt such as acetate and methane sulfonate; an alkali metal salt such as sodium salt and potassium salt; an alkaline earth metal salt such as magnesium salt and calcium salt; and an organic amine salt such as triethanolamine salt and tris(hydroxymethyl)aminomethane salt. Among the isoindole derivatives represented by the general formula (I') or (I''), a compound wherein X or X' is an amino group or a hydroxyl group (and/or a compound wherein R' or R'' has an amino group or a hydroxyl group as a substituent), may also form a salt. The salt may be any salt so long as it is pharmaceutically acceptable. For example, it includes salts as mentioned above.

In the constituting component

of the general formula (I') and (I''), one asymmetric carbon atom exists, and thus an optically active substance of S-form or R-form exists. In the present invention, the isoindole derivative represented by the general formula (I') and (I''), or its salt, includes a racemic modification, the S-form or the R-form, unless otherwise specified.

In the general formula (I'), the racemic modifications, the optically active substances of S-form or R-form of the following compounds are preferred.

(1) A compound wherein Z' is a methyl group, R' is a phenyl group, a naphthyl group or a cyclohexyl group, X is a nitro group or a halogen atom, Y is an oxygen atom, $Q_3$ is —C(O)— or —C(S)—, and m is 0, 1 or 4.

(2) A compound wherein Z' is a methyl group, R' is a phenyl group, a naphthyl group or a cyclohexyl group, X is a fluorine atom, Y is an oxygen atom, $Q_3$ is —C(O)— or —C(S)—, and m is 0 or 4.

(3) A compound wherein Z' is a methyl group, R' is a phenyl group, a naphthyl group or a cyclohexyl group, X is a fluorine atom, Y is an oxygen atom, $Q_3$ is —C(O)—, and m is 0 or 4.

In the general formula (I"), the racemic modifications, the optically active substances of S-form or R-form of the following compounds are more preferred.

(1) A compound wherein Z' is a methyl group, R" is a phenyl group, a naphthyl group or a cyclohexyl group, X' is a nitro group or a halogen atom, Y is an oxygen atom, A is an oxygen atom or a sulfur atom, m is 0, 1 or 4, and n is 1.

(2) A compound wherein Z' is a methyl group, R" is a phenyl group, a naphthyl group or a cyclohexyl group, X' is a fluorine atom, Y is an oxygen atom, A is an oxygen atom or a sulfur atom, m is 0 or 4, and n is 1.

(3) A compound wherein Z' is a methyl group, R" is a phenyl group, a naphthyl group or a cyclohexyl group, X' is a fluorine atom, Y and A are oxygen atoms, m is 0 or 4, and n is 1.

Further, in the general formula (I'), the following compounds are more preferred.

(4) (R)-2-(1-phenylethyl)-1H-isoindole-1,3-dione, (R)-2-(1-naphthylethyl)-1H-isoindole-1,3-dione, (R)-2-(1-phenylethyl)-4,5,6,7-tetrafluoro-1H-isoindole-1,3-dione, (R)-2-(1-naphthylethyl)-4,5,6,7-tetrafluoro-1H-isoindole-1,3-dione, (R)-2-(1-cyclohexylethyl)-1H-isoindole-1,3-dione, (R)-2-(1-cyclohexylethyl)-4,5,6,7-tetrafluoro-1H-isoindole-1,3-dione, (R)-2-(1-phenylethyl)-1H-isoindole-1-thio-3-one, (R)-2-(1-naphthylethyl)-1H-isoindole-1-thio-3-one, (R)-2-(1-phenylethyl)-4,5,6,7-tetrafluoro-1H-isoindole-1-thio-3-one, (R)-2-(1-naphthylethyl)-4,5,6,7-tetrafluoro-1H-isoindole-1-thio-3-one, (R)-2-(1-cyclohexylethyl)-1H-isoindole-1-thio-3-one or (R)-2-(1-cyclohexylethyl)-4,5,6,7-tetrafluoro-1H-isoindole-1-thio-3-one.

Further, in the general formula (I), the following compounds are most preferred.

(5) (R)-2-(1-phenylethyl)-1H-isoindole-1,3-dione, (R)-2-(1-naphthylethyl)-1H-isoindole-1,3-dione, (R)-2-(1-phenylethyl)-4,5,6,7-tetrafluoro-1H-isoindole-1,3-dione, (R)-2-(1-naphthylethyl)-4,5,6,7-tetrafluoro-1H-isoindole-1,3-dione, (R)-2-(1-cyclohexylethyl)-1H-isoindole-1,3-dione or (R)-2-(1-cyclohexylethyl)-4,5,6,7-tetrafluoro-1H-isoindole-1,3-dione.

As the N-phenylimide compound of the general formula (I'''-1) or (I'''-2) or its salt, the preferred is as follows:

(1) Both $R_1$ and $R_2$ are isopropyl groups.

(2) $X_1$ or $X_2$ is a fluorine atom or a nitro group.

(3) Each of m and p is 0 or 1.

(4) $Q_5$ is —C(O)—.

The cyclic imide derivative of the general formula (I) or its salt of the present invention (hereinafter referred to as the compound of the present invention for short) can be produced by various methods. For example, the compound of the present invention can be produced by methods [A] to [C] as shown hereinafter or by conventional salt-forming reactions. Further, as the case requires, by modifying the substituent of the compound thus obtained or converting the substituent to another substituent, the compound can be converted to a compound having the corresponding substituent. As such a treatment, acylation of an amino acid or reduction of a nitro group, may, for example, be mentioned.

[A] In a case where $Q_2$ is —C(O)— and $Q_3$ is —CH₂—, or $Q_2$ is —CH₂— and $Q_3$ is —C(O)—:

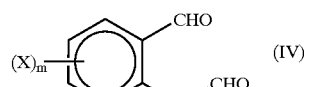

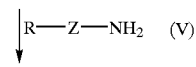

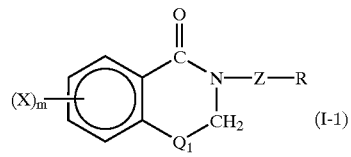

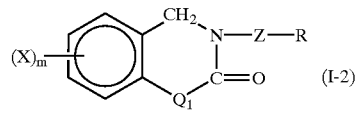

wherein $Q_1$, Z, R, X and m are as defined above.

[B] In a case where $Q_2$ is —C(O)— and $Q_3$ is —C(O)—:

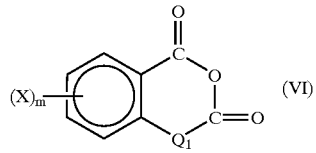

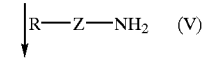

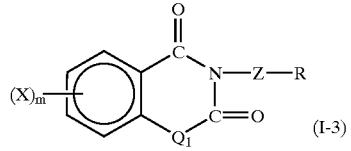

wherein $Q_1$, Z, R, X and m are as defined above.

[C] In a case where $Q_2$ is —C(S)—:

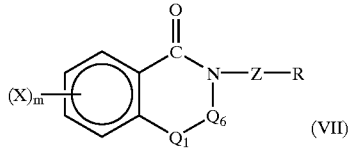

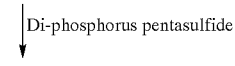

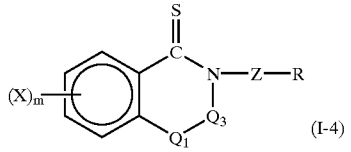

wherein $Q_3$, Z, R, X and m are as defined above, and $Q_6$ is —C(O)— or —CH₂—.

The reaction [A] will be described below.

The reaction [A] is usually conducted in the presence of an acid substance. As the acid substance, one or more are suitably selected from the group consisting of organic acids such as acetic acid and toluene sulfonic acid, and inorganic acids such as sulfuric acid and hydrochloric acid.

The reaction [A] is conducted in the presence of a solvent, as the case requires. The solvent may be any solvent so long as it is inert to the reaction. It may, for example, be an aromatic hydrocarbon such as benzene, toluene, xylene or chlorobenzene; a cyclic or non-cyclic aliphatic hydrocarbon such as carbon tetrachloride, methylene chloride, chloroform, dichloromethane, dichloroethane, trichloroethane, hexane or cyclohexane; an ether such as dioxane; a polar aprotic solvent such as dimethylsulfoxide, dimethylacetamide, dimethylformamide or N-methylpyrrolidone; or an organic acid such as acetic acid. One or more of them are suitably selected.

The reaction temperature of the reaction [A] varies depending upon the reaction condition, and can not be absolutely defined. It is usually from 0 to 80° C., preferably from 20 to 40° C. The reaction time is usually from 0.1 to 4 hours, preferably from 0.2 to 2 hours.

The reaction [B] will be described below.

The reaction [B] is conducted in the presence of a solvent, as the case requires. The solvent may be any solvent so long as it is inert to the reaction. It may, for example, be an aromatic hydrocarbon such as benzene, toluene, xylene or chlorobenzene; an ether such as dioxane; a polar aprotic solvent such as dimethylsulfoxide, dimethylacetamide or N-methylpyrrolidone. One or more of them are suitably selected.

The reaction temperature of the reaction [B] varies depending upon the reaction condition, and can not be absolutely defined. It is usually from 100 to 200° C., preferably from 140 to 200° C. The reaction time is usually from 1 to 4 hours, preferably from 1 to 2 hours.

The reaction [C] will be described below.

The reaction [C] is conducted in the presence of a solvent, as the case requires. The solvent may be any solvent so long as it is inert to the reaction. It may, for example, be an aromatic hydrocarbon such as benzene, toluene, xylene or chlorobenzene; an ether such as dioxane; or a polar aprotic solvent such as dimethylsulfoxide, dimethylacetamide or N-methylpyrrolidone. One or more of them are suitably selected.

The reaction temperature of the reaction [C] varies depending upon the reaction condition, and can not be absolutely defined. It is usually from 100 to 200° C., preferably from 120 to 180° C. The reaction time is usually from 0.5 to 40 hours, preferably from 1 to 40 hours.

In the reaction [C], as di-phosphorus pentasulfide, di-phosphorus pentasulfide itself or its dimer may be used. Further, in the reaction [C], by employing an optional reaction condition, it is possible to selectively produce monothio type, or to produce a mixture of monothio type and dithio type. In the case where the mixture of monothio type and dithio type is obtained, it is possible to separate them by purification means such as column separation.

The isoindole derivative represented by the general formula (I') or its salt can be produced by the methods [A'] to [C'] as shown hereinafter or by conventional salt-forming reactions.

[A'] In a case where Y is an oxygen atom and $Q_3$ is —$CH_2$—:

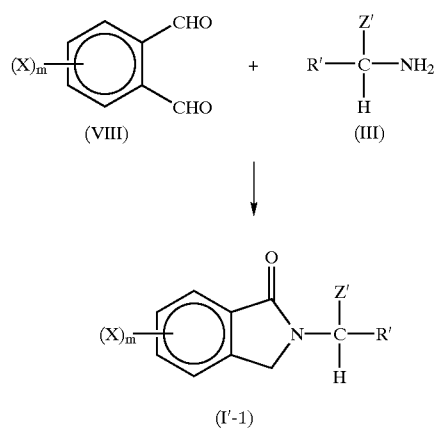

[B'] In a case where Y is an oxygen atom and $Q_3$ is —C(O)—:

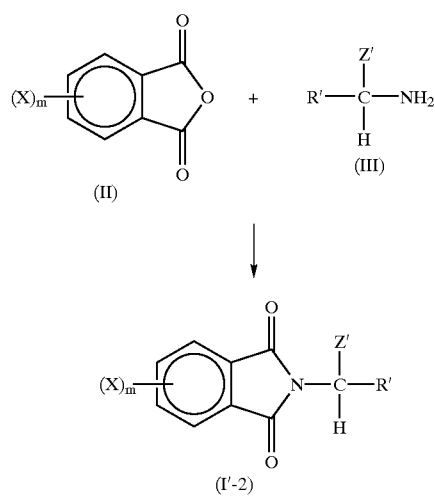

[C'] In a case where Y is a sulfur atom:

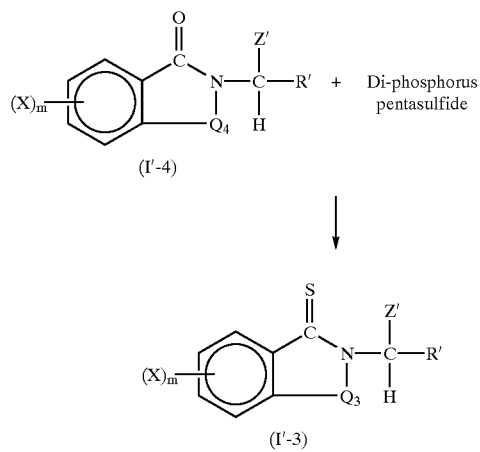

In an amine represented by the general formula (III):

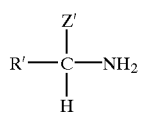

one asymmetric carbon atom exists, and thus an optically active substance of S-form or R-form exists. The amine includes a racemic modification, the S-form or R-form, unless otherwise specified.

The reaction [A'] can be conducted in the same manner as the reaction [A]. In the reaction [A'], Z', R', X and m are as defined above.

The reaction [B'] can be conducted in the same manner as the reaction [B]. In the reaction [B'], Z', R', X and m are as defined above.

The reaction [C'] can be conducted in the same manner as the reaction [C]. In the reaction [C'], Z', R', X and m are as defined above, $Q_3$ is —C(O)—, —C(S)— or —CH$_2$—, and $Q_4$ is —C(O)— or —CH$_2$—.

The N-phenylimide compound of the general formula (I'''-1) or (I'''-2) or its salt of the present invention, can be produced by various methods. For example, the N-phenylimide compound or its salt of the present invention can be produced by the following reaction.

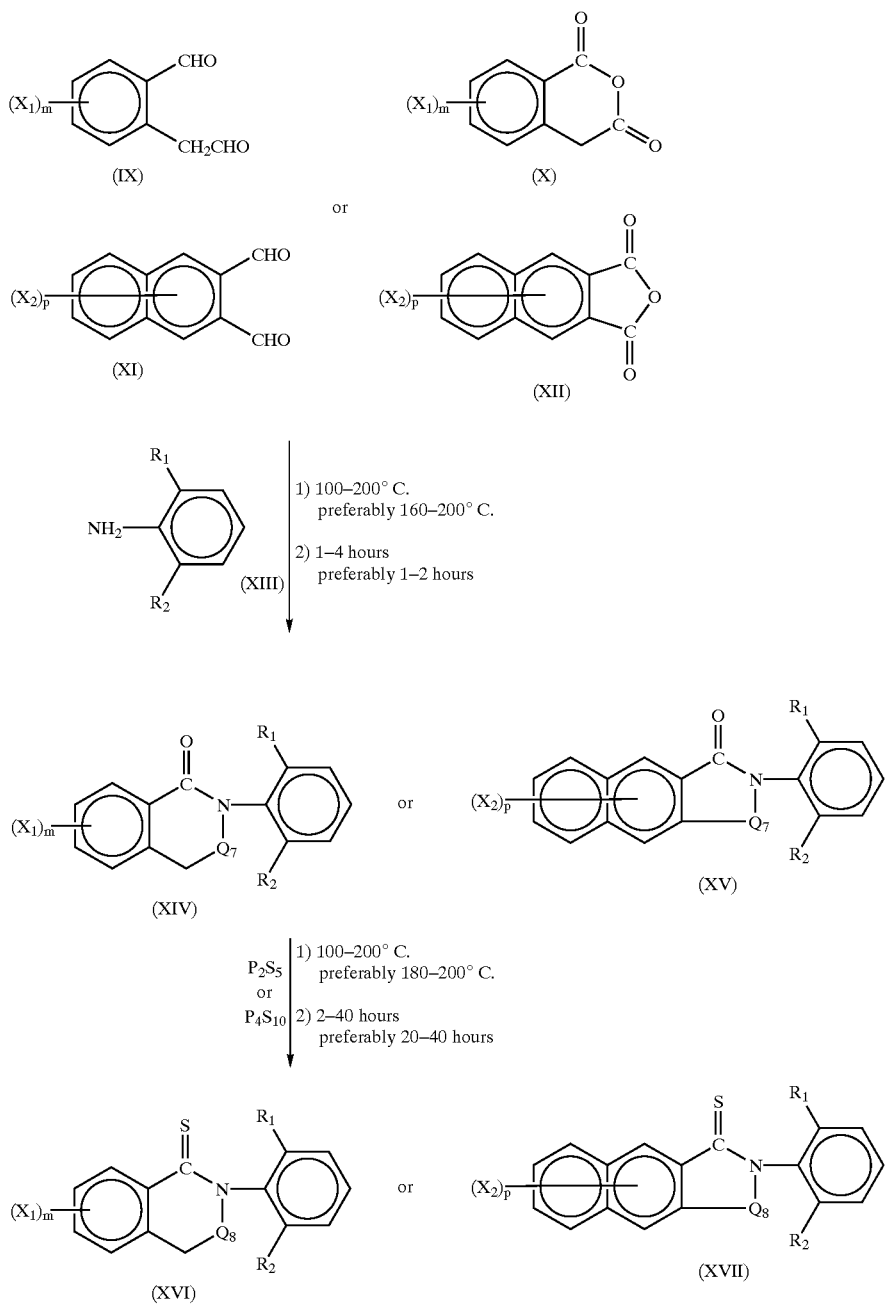

wherein $R_1$, $R_2$, $X_1$, $X_2$, m and p are as defined above, $Q_7$ is —C(O)— or —CH$_2$—, and $Q_8$ is —C(O)— or —CH$_2$—.

With regard to the N-phenylimide compound represented by the general formula (I'''-1) or (I'''-2), one having an oxygen atom as Y, is produced by the former step of the reaction, and one having a sulfur atom as Y, is produced by the latter step of the reaction. In the latter step of the reaction, it is possible to produce compounds represented by the following general formulae as well as the general formula (I'''-3) or (I'''-4). By employing optional reaction conditions, these compounds may be produced selectively or as a mixture. In the case where they are produced as a mixture, it is possible to separate them by purification means such as column separation.

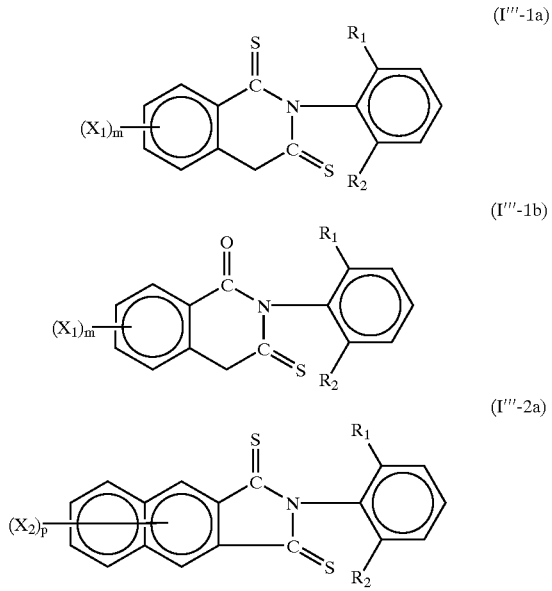

(I'''-1a)

(I'''-1b)

(I'''-2a)

The reaction of the compound represented by the general formula (IX) or (XI) with the aniline compound represented by the general formula (XIII) is conducted in the same manner as the reaction [A].

The reaction of the compound represented by the general formula (IX), (X), (XI) or (XII) with an aniline compound represented by the general formula (XIII), can be conducted in the presence of an inert solvent, or may be conducted in a molten state without using a solvent. The inert solvent may, for example, be an aromatic hydrocarbon such as benzene, toluene, xylene or chlorobenzene; an ether such as dioxane; a polar aprotic solvent such as dimethylsulfoxide, dimethylacetamide or N-methylpyrrolidone. One or more of them are suitably selected. The reaction of the imide compound represented by the general formula (XIV) or (XV) with phosphorus pentasulfide or its dimer, is usually conducted in the presence of an inert solvent, and the inert solvent is as defined above.

The compound of the general formula (I'''-2) may form a salt as well as the compound of the general formula (I'''-1) of the present invention. Further, it is also useful as an active ingredient of a pharmaceutical composition. It has bioactivities as explained with regard to the compound of the general formula (I'''-1), which will be explained hereinafter.

The phthalimide derivative represented by the general formula (I'''') or its salt can be produced by methods [A] to [C], by using e.g. R''''—NH$_2$ as R—Z—NH$_2$.

The N-phenylphthalimide derivative can be made by various methods. Among these, N-phenylphthalimide can be produced by reacting phthalic anhydride with aniline as shown by the reaction [A]. Further, N-phenylthiophthalimide can be produced by reacting N-phenylphthalimide with di-phosphorus pentasulfide or one having the same function as its dimer, as shown by the reaction [C].

In this case, it is possible to conduct the reaction [A] in the presence of an acid substance as mentioned above, and it is also possible to use an excess amount of phthalic anhydride. In the case where a solvent is used in the reaction, an aromatic hydrocarbon, an ether or a polar aprotic solvent as mentioned above, is preferably used. The reaction temperature of the reaction [A] varies depending upon the reaction condition, and can not be absolutely defined. It is usually from 100 to 200° C., preferably from 140 to 200° C. The reaction time is usually from 1 to 4 hours, preferably from 1 to 2 hours.

In a case where the solvent is used in the reaction [C], the same solvent as mentioned in the reaction [A] is preferably used. The reaction temperature of the reaction [C] varies depending upon the reaction condition, and can not be absolutely defined. It is usually from 100 to 200° C., preferably from 120 to 180° C. The reaction time is usually from 0.5 to 40 hours, preferably from 1 to 40 hours.

In one of other modes, the present invention provides an N-phenylphthalimide derivative represented by the general formula (I''''):

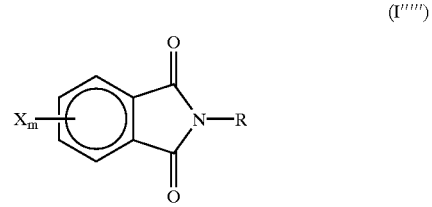

(I'''')

wherein R is an aryl group which may be substituted, such as a phenyl group which may be substituted, provided that the substituent may, for example, be a nitro group or an amino group which may be acylated such as an amino group or a lower acylamino group, an alkoxy group, an alkylthio group or an alkyl group, X is a nitro group, an amino group which may be acylated, a cyano group, a trifluoromethyl group, a hydroxyl group, a halogen atom, an alkyl group, an alkoxy group or an alkylthio group, and m is an integer of from 0 to 4, provided that when m is 2 or above, X may be the same or different, or its salt, a method for producing it, and a pharmaceutical composition comprising it. According to the present invention, an aminopeptidase N inhibitor and an angiogenesis inhibitor, and further, a TNF-α production modulator such as a TNF- a production inhibitor or a TNF-αproduction enhancer, which comprises an N-phenylphthalimide derivative represented by the general formula (I'''') or its salt, and a pharmaceutically acceptable carrier, can be provided.

The compound of the present invention is useful as an active ingredient of a pharmaceutical composition. Particularly, it has effect to modulate (enhance or suppress) production of tumor necrosis factor (TNF-α), anti-angiogenetic activity and/or aminopeptidase N inhibitory activity. Therefore, it can be effectively used to treat or prevent various diseases. Among these, an optically active substance of R-form of the compound represented by the general formula (I') or its salt suppresses production of tumor necrosis factor well, and thus it can be effectively used to treat or prevent various diseases.

(Effect of Modulating TNF-αProduction)

TNF-α has been known as a cytokine which widely relates to control of biological responses by means of inflammation and immuno reactions, with various activities such that it has desirable effects such as cytotoxicity against tumor cells, activation of T cells which is one of immuno cells, activation of anti-tumor macrophages, activation of neutrophils, induction of interferon-$β_2$ by fibroblasts and stimulation of immuno systems, while excessive production of TNF-α causes undesirable effects such as acceleration of cancer metastasis and angiogenesis, induction of endotoxin shock, induction of inflammation of organs and tissues, inhibition of lipoprotein lipase of adipocytes, and induction of replication of human immuno deficiency viruses. The pharmaceutical composition which comprises the compound of the present invention is a biological response modulator which makes it possible to modulate the amount of TNF-α in the body. It can be used as an immunostimulant which is effective for treatment of diseases such as cancer, and as an immunosuppressant which has therapeutic effect against transplant graft rejection, graft versus host diseases or immune diseases. It also has therapeutic effect against other diseases which relate to TNF-α. As the immune diseases, autoimmune diseases such as rheumatic fever and rheumatoid arthritis, erythema nodosum leprosum, Behchet's diseases, lupus erythematosus and aphthous ulcer may, for example, be mentioned. As the other diseases which relate to TNF-α, cachexia in cancer or infectious diseases, septic shock, adult respiratory distress syndrome, osteoarthritis, multiple sclerosis, inflammatory enteropathy, multiple organ failure, malaria, meningitidis, hepatitis, diabetes and acquired immunodeficiency syndrome may, for example, be mentioned. Further, in the case where the amount of TNF-α increases excessively by e.g. cancer treatment, by using the pharmaceutical composition which comprises the compound of the present invention together, it is possible to suppress side effects by excessive TNF-α induced.

(Inhibition of Angiogenesis)

It has been known that excessive activation of angiogenesis relates to onset or progression step of various diseases. As the diseases, specifically, cancer and cancer metastasis; benign tumors such as angioma, auditory neuroma, neurofibroma, trachoma, purulent granuloma and granulation; chronic inflammatory diseases such as rheumatoid arthritis; psoriasis; eye diseases relating to angiogenesis, such as diabetic retinopathy, retinopathy of prematurity, macular degeneration, glaucoma, retrolental fibroplasia and central retinal vein atresia; angiogenesis resulting from corneal transplantation; hypertrophic scar; atherosclerosis; scleredema; and nephropathy may, for example, be mentioned. The pharmaceutical composition which comprises the compound of the present invention can be used as an angiogenesis inhibitor, and it is useful as a preventive drug or a therapeutic drug for such diseases.

(Inhibition of Aminopeptidase N)

Aminopeptidase N is an enzyme which hydrolyzes peptides, as substrates, having e.g. alanine, leucine, phenylalanine, tyrosine, arginine, methionine, lysine, tryptophan, glycine, serine or histidine, at the amino terminal. Aminopeptidase N is distributed mainly in epithelial cells of kidney and small intestine, monocytes or granulocytes, cancer cells and on cell surface membrane of placenta, liver and pancreas. Its various physiological functions such as digestion and absorption of amino acids, biosyntheses and degradation of peptide hormones, growth factors and autacoids and degradation of extracellular matrix, have been studied (Ketsueki, Shuyo-ka, vol. 29, 288–296, 1994). Further, relation of the enzyme to immune functions has been indicated (Japanese Journal of Cancer and Chemotherapy, vol. 9, 1019–1024, 1982). Further, it was reported that inhibition of aminopeptidase N suppresses metastasis of cancer cells (Cancer Research, vol. 46, 4505–4510, 1986). The pharmaceutical composition which comprises the compound of the present invention can be used as an aminopeptidase N inhibitor, and it is useful as a preventive drug or a therapeutic drug for cancer, cancer metastasis, inflammatory diseases, autoimmune diseases or allergic diseases.

Particularly preferred modes are as follows:.

(1) An angiogenesis inhibitor which comprises, as an active ingredient, the cyclic imide derivative represented by the general formula (I).

(2) An aminopeptidase N inhibitor which comprises, as an active ingredient, the cyclic imide derivative represented by the general formula (I).

(3) An biological response modulator which comprises, as an active ingredient, the isoindole derivative represented by the general formula (I').

(4) An immunostimulant which comprises, as an active ingredient, the isoindole derivative represented by the general formula (I').

(5) An immunosuppressant which comprises, as an active ingredient, the isoindole derivative represented by the general formula (I').

(6) A TNF-α production enhancer which comprises, as an active ingredient, the isoindole derivative represented by the general formula (I').

(7) A TNF-α production suppressor which comprises, as an active ingredient, the isoindole derivative represented by the general formula (I').

(8) An anticancer agent which comprises, as an active ingredient, the isoindole derivative represented by the general formula (I').

(9) An anti-inflammatory agent which comprises, as an active ingredient, the isoindole derivative represented by the general formula (I').

(10) An anti-diabetic agent which comprises, as an active ingredient, the isoindole derivative represented by the general formula (I').

(11) An angiogenesis inhibitor which comprises, as an active ingredient, the isoindole derivative represented by the general formula (I').

(12) An anti-rheumatic agent which comprises, as an 15 active ingredient, the isoindole derivative represented by the general formula (I').

(13) An angiogenesis inhibitor which comprises, as an active ingredient, the N-phenyl imide compound represented by the general formula (I'''-1) or (I'''-2).

(14) An aminopeptidase N inhibitor which comprises, as an active ingredient, the N-phenyl imide compound represented by the general formula (I'''-1) or (I'''-2).

(15) An angiogenesis inhibitor which comprises, as an active ingredient, the phthalimide derivative represented by the general formula (I'''').

(16) An aminopeptidase N inhibitor which comprises, as an active ingredient, the phthalimide derivative represented by the general formula (I'''').

(17) An angiogenesis inhibitor which comprises, as an active ingredient, the N-phenyl phthalimide derivative represented by the general formula (I'''').

(18) An aminopeptidase N inhibitor which comprises, as an active ingredient, the N-phenyl phthalimide derivative represented by the general formula (I'''').

When the compound of the present invention is administered as the pharmaceutical composition, it is administered usually alone or in admixture with various pharmaceutically acceptable formulation adjuvants, in the form of a drug formulation suitable for peroral, parenteral, topical or per rectal use, such as a tablet, a capsule, a powder, a granule, an injection drug, a liquid formulation, a syrup, a suspension, an ophthalmic solution, an inhalant, an ointment or a suppository.

As the formulation suitable for peroral use, a solid composition such as a tablet, a capsule, a powder, a granule or a troach, or a liquid composition such as a liquid formulation, a syrup or a suspension may, for example, be mentioned. To formulate the solid composition, as the formulation adjuvant, a binder such as carboxymethyl cellulose, gum arabic, tragacanth gum, calcium carbonate, gelatin, polyvinylpyrrolidone, water, ethanol, glucose solution or starch solution; an excipient such as starch, lactose, sucrose, glucose, sodium chloride, calcium carbonate, carboxymethyl cellulose or silicic acid; a disintegrator such as alginic acid, starch, carboxymethyl cellulose, sodium carboxymethyl cellulose; a lubricant such as magnesium stearate, light silicic anhydride or urea; a surface active agent such as a polyoxyethylene sorbitan fatty acid ester or an alkylsulfate; a capsule base such as gelatin; or a sweetener, a flavoring agent, a disintegration inhibitor, an absorption accelerator, a stabilizer, a preservative or a thickener can be used. To formulate the liquid composition, as the formulation adjuvant, sorbitol, gelatin, methyl cellulose, carboxymethyl cellulose or a vegetable oil, and further emulsifying agent, a sweetener, a flavoring agent, an absorption accelerator, a stabilizer or a preservative can be used. It is formulated so that the compound of the present invention is contained usually in an amount of from 0.1 to 95 wt %.

As the formulation suitable for parenteral use, an injecting drug may, for example, be mentioned. To formulate an injecting drug, by using a carrier such as distilled water or isotonic sodium chloride solution, the compound is formulated into a form to be injected, such as a suspension or an emulsion. In this case, a pharmaceutically acceptable buffer or a reagent to modulate osmotic pressure, such as benzyl alcohol as a preservative or ascorbic acid as an antioxidant, may be contained. The injection drug is formulated so that the compound of the present invention is contained usually in an amount of from 0.1 to 10 wt %.

As the formulation suitable for topical or per rectal use, an ophthalmic solution, an inhalant, an ointment or a suppository may, for example, be mentioned. The ophthalmic solution is formulated by the conventional method by using a pharmaceutically acceptable carrier. When the compound of the present invention is administered as an inhalant, it is administered to respiratory organs in a form such that the compound of the present invention itself or with a pharmaceutically acceptable inert carrier is dissolved in a solution for an aerosol or a nebulizer, or in a form of a fine powder for inhalation. An ointment is formulated by the conventional method by adding e.g. a base which is usually used. It is formulated so that the compound of the present invention is contained usually in an amount of from about 0.1 to about 30 wt %. A suppository is formulated by the conventional method by using a carrier which is known in the filed, such as polyethyleneglycol, lanolin, cacao butter or fatty acid triglyceride. It is formulated so that the compound of the present invention is contained usually in an amount of from about 0.1 to about 95 wt %.

EXAMPLES

Now, the present invention will be described in further detail with reference to Examples. However, the present invention is by no means restricted by such Examples. First, synthesis Examples of the compounds of the present invention will be described.

Synthesis Example 1

Synthesis of (R)-2-(1-phenylethyl)-4,5,6,7-tetrafluoro-1H-isoindole-1,3-dione (Compound No.18)

220 mg of tetrafluorophthalic anhydride and 121 mg of (R)-α-methylbenzylamine were charged in an egg-plant type flask of 50 ml, followed by stirring under heating at a temperature of 180° C. for 2 hours. After cooled, the reaction product was dissolved in chloroform, purified by silica gel column chromatography (eluent; methylene chloride:methanol=30:1 v/v), recrystallized from a mixed solvent of n-hexane-ethyl acetate, to obtain 210 mg of the desired product as colorless needles. Yield: 65%. m.p. 95.5–96° C.; $[\alpha]^{20}_D$=41.5° (C=0.348 AcOEt); MS(EI+) 323 (M)$^+$ Synthesis Example 2

Synthesis of (S)-2-(1-phenylethyl)-4,5,6,7-tetrafluoro-1H-isoindole-1,3-dione (Compound No.17)

220 mg of tetrafluorophthalic anhydride and 121 mg of (S)-α-methylbenzylamine were charged in an egg-plant type flask of 50 ml, followed by stirring under heating at a temperature of 180° C. for 2 hours. After cooled, the reaction product was dissolved in chloroform, purified by silica gel column chromatography (eluent; methylene chloride:methanol=30:1 v/v), recrystallized from a mixed solvent of n-hexane-ethyl acetate, to obtain 240 mg of the desired product as colorless needles. Yield: 74%. m.p. 95–96° C.; $[\alpha]^{20}_D$=−42.2° (C=0.386 AcOEt); MS(EI+) 323 (M)$^+$ Synthesis Example 3

Synthesis of (R)-2-(1-naphthylethyl)-4,5,6,7-tetrafluoro-1H-isoindole-1,3-dione (Compound No.50)

220 mg of tetrafluorophthalic anhydride and 121 mg of (R)-α-methylbenzylamine were charged in an egg-plant type flask of 50 ml, followed by stirring under heating at a temperature of 180° C. for 2 hours. After cooled, the reaction product was dissolved in chloroform, purified by silica gel column chromatography (eluent; methylene chloride:methanol=30:1 v/v), and further purified by Kugelrohr distillation, to obtain 290 mg of the desired product as yellow oil (when it was left at room temperature, it was solidified). Yield: 78%. b.p. 240° C. (1 mmHg); $[\alpha]^{20}_D$= 40.9° (C=0.089 EtOH); MS(EI+) 373(M)$^+$ Synthesis Example 4

Synthesis of (S)-2-(1-naphthylethyl)-4,5,6,7-tetrafluoro-1H-isoindole-1,3-dione (Compound No.49)

220 mg of tetrafluorophthalic anhydride and 121 mg of (S)-α-methylbenzylamine were charged in an egg-plant type flask of 50 ml, followed by stirring under heating at a temperature of 180° C. for 2 hours. After cooled, the reaction product was dissolved in chloroform, purified by silica gel column chromatography (eluent; methylene chloride:methanol=30:1 v/v), and further purified by Kugelrohr distillation, to obtain 280 mg of the desired product as yellow oil (when it was left at room temperature, it was solidified). Yield: 75%. b.p. 240° C. (1 mmHg); $[\alpha]^{20}{}_D$=−42.1° (C=0.097 EtOH); MS(EI+) 373(M)$^+$ Synthesis Example 5

Synthesis of (R)-2-(1-cyclohexylethyl)-4,5,6,7-tetrafluoro-1H-isoindole-1,3-dione (Compound No.69)

220 mg of tetrafluorophthalic anhydride and 127 mg of (R)-α-methylbenzylamine were charged in an egg-plant type flask of 50 ml, followed by stirring under heating at a temperature of 180° C. for 1.5 hours. After cooled, the reaction product was dissolved in chloroform, purified by silica gel column chromatography (eluent; methylene chloride:methanol=30:1 v/v), recrystallized from a mixed solvent of n-hexane-ethyl acetate, to obtain 210 mg of the desired product as a colorless powder. Yield: 64%. m.p. 147–148° C.; $[\alpha]^{20}{}_D$=−5.13° (C=0.658 AcOEt); MS(EI+) 329(M)$^+$ Synthesis Example 6

Synthesis of (S)-2-(1-cyclohexylethyl)-4,5,6,7-tetrafluoro-1H-isoindole-1,3-dione (Compound No.68)

220 mg of tetrafluorophthalic anhydride and 127 mg of (S)-α-methylbenzylamine were charged in an egg-plant type flask of 50 ml, followed by stirring under heating at a temperature of 180° C. for 1.5 hours. After cooled, the reaction product was dissolved in chloroform, purified by silica gel column chromatography (eluent; methylene chloride:methanol=30:1 v/v), recrystallized from a mixed solvent of n-hexane-ethyl acetate, to obtain 215 mg of the desired product as a colorless powder. Yield: 65%. m.p. 147–148° C.; $[\alpha]^{20}{}_D$=5.26° (C=0.618 AcOEt); MS(EI+) 329(M)$^+$ Synthesis Example 7

Synthesis of (R)-2-(1-phenylethyl)-4-nitro-1H-isoindole-1,3-dione (Compound No.84)

386 mg of 3-nitrophthalic anhydride and 242 mg of (R)-α-methylbenzylamine were charged in an egg-plant type flask of 50 ml, followed by stirring under heating at a temperature of 180° C. for 1.5 hours. After cooled, the reaction product was dissolved in chloroform, purified by silica gel column chromatography (eluent; methylene chloride:methanol=30:1 v/v), recrystallized from a mixed solvent of n-hexane-ethyl acetate, to obtain 430 mg of the desired product as a light yellow powder. Yield: 73%. m.p. 115–117° C.; MS(EI+) 296(M)$^+$ Synthesis Example 8

Synthesis of (S)-2-(1-phenylethyl)-4-nitro-1H-isoindole-1,3-dione (Compound No.83)

386 mg of 3-nitrophthalic anhydride and 242 mg of (S)-α-methylbenzylamine were charged in an egg-plant type flask of 50 ml, followed by stirring under heating at a temperature of 180° C. for 1.5 hours. After cooled, the reaction product was dissolved in chloroform, purified by silica gel column chromatography (eluent; methylene chloride:methanol=30:1 v/v), recrystallized from a mixed solvent of n-hexane-ethyl acetate, to obtain 443 mg of the desired product as a light yellow powder. Yield: 75%. m.p. 115–117° C.; MS(EI+) 296(M)$^+$ Representative examples of the compounds of the present invention synthesized based on the Synthesis Examples or the methods for producing the compounds of the present invention as mentioned above, are listed in Table 1.

TABLE 1

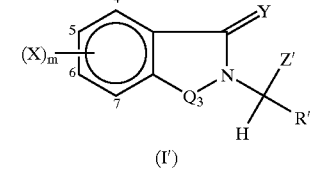

(I')

| Comp. No. | R' | (X)$_m$ | Z' | Y | Q$_3$ | Physical properties (mp: °C.) |
|---|---|---|---|---|---|---|
| 1 | Phenyl group | — (m = 0; the same applies hereinafter) | CH$_3$ | O | CH$_2$ | Racemic modification |
| 2 | Phenyl group | — | " | O | CH$_2$ | S-form |
| 3 | Phenyl group | — | " | O | CH$_2$ | R-form |
| 4 | Phenyl group | 4,5,6,7-F$_4$ | " | O | CH$_2$ | Racemic modification |
| 5 | Phenyl group | 4,5,6,7-F$_4$ | " | O | CH$_2$ | S-form |
| 6 | Phenyl group | 4,5,6,7-F$_4$ | " | O | CH$_2$ | R-form |
| 7 | Phenyl group | 4,5,6,7-Cl$_4$ | " | O | CH$_2$ | Racemic modification |
| 8 | Phenyl group | 4,5,6,7-Cl$_4$ | " | O | CH$_2$ | S-form |
| 9 | Phenyl group | 4,5,6,7-Cl$_4$ | " | O | CH$_2$ | R-form |
| 10 | Phenyl group | — | " | O | C=O | Racemic modification |
| 11 | Phenyl group | — | " | O | C=O | S-form |
| 12 | Phenyl group | — | " | O | C=O | R-form |
| 13 | Phenyl group | 4-OH | " | O | C=O | Racemic modification |
| 14 | Phenyl group | 4-OH | " | O | C=O | S-form |
| 15 | Phenyl group | 4-OH | " | O | C=O | R-form |
| 16 | Phenyl group | 4,5,6,7-F$_4$ | " | O | C=O | Racemic modification |
| 17 | Phenyl group | 4,5,6,7-F$_4$ | " | O | C=O | S-form 95~96 |
| 18 | Phenyl group | 4,5,6,7-F$_4$ | " | O | C=O | R-form 95.5~96 |
| 19 | Phenyl group | 4,5,6,7-Cl$_4$ | " | O | C=O | Racemic modification |
| 20 | Phenyl group | 4,5,6,7-Cl$_4$ | " | O | C=O | S-form |
| 21 | Phenyl group | 4,5,6,7-Cl$_4$ | " | O | C=O | R-form |
| 22 | Phenyl group | 5-OH | " | O | C=O | Racemic modification |
| 23 | Phenyl group | 5-OH | " | O | C=O | S-form |

TABLE 1-continued

| Comp. No. | R' | (X)$_m$ | Z' | Y | Q$_3$ | Physical properties (mp: °C.) |
|---|---|---|---|---|---|---|
| 24 | Phenyl group | 5-OH | " | O | C=O | R-form |
| 25 | Phenyl group | 4,5,6,7-F$_4$ | " | S | C=O | Racemic modification |
| 26 | Phenyl group | 4,5,6,7-F$_4$ | " | S | C=O | S-form |
| 27 | Phenyl group | 4,5,6,7-F$_4$ | " | S | C=O | R-form |
| 28 | Phenyl group | 4,5,6,7-Cl$_4$ | " | S | C=O | Racemic modification |
| 29 | Phenyl group | 4,5,6,7-Cl$_4$ | " | S | C=O | S-form |
| 30 | Phenyl group | 4,5,6,7-Cl$_4$ | " | S | C=O | R-form |
| 31 | Phenyl group | — | " | S | C=O | Racemic modification |
| 32 | Phenyl group | — | " | S | C=O | S-form |
| 33 | Phenyl group | — | " | S | C=O | R-form |
| 34 | Phenyl group | 4-CN | " | O | C=O | Racemic modification |
| 35 | Phenyl group | 4-CN | " | O | C=O | S-form |
| 36 | Phenyl group | 4-CN | " | O | C=O | R-form |
| 37 | Phenyl group | 4-CF$_3$ | " | O | C=O | Racemic modification |
| 38 | Phenyl group | 4-CF$_3$ | " | O | C=O | S-form |
| 39 | Phenyl group | 4-CF$_3$ | " | O | C=O | R-form |
| 40 | Phenyl group | 4,5,6,7-F$_4$ | " | S | C=S | Racemic modification |
| 41 | Phenyl group | 4,5,6,7-F$_4$ | " | S | C=S | S-form |
| 42 | Phenyl group | 4,5,6,7-F$_4$ | " | S | C=S | R-form |
| 43 | Phenyl group | 4,5,6,7-Cl$_4$ | " | S | C=S | Racemic modification |
| 44 | Phenyl group | 4,5,6,7-Cl$_4$ | " | S | C=S | S-form |
| 45 | Phenyl group | 4,5,6,7-Cl$_4$ | " | S | C=S | R-form |
| 46 | 1-naphthyl group | — | " | O | C=O | Racemic modification |
| 47 | 1-naphthyl group | — | " | O | C=O | S-form |
| 48 | 1-naphthyl group | — | " | O | C=O | R-form |
| 49 | 1-naphthyl group | 4,5,6,7-F$_4$ | " | O | C=O | S-form: bp. 240° C./1 mmHg |
| 50 | 1-naphthyl group | 4,5,6,7-F$_4$ | " | O | C=O | R-form: bp. 240° C./1 mmHg |
| 51 | 1-naphthyl group | 4,5,6,7-F$_4$ | " | O | C=O | Racemic modification |
| 52 | 1-naphthyl group | — | " | S | C=O | Racemic modification |
| 53 | 1-naphthyl group | — | " | S | C=O | S-form |
| 54 | 1-naphthyl group | — | " | S | C=O | R-form |
| 55 | 1-naphthyl group | 4,5,6,7-Cl$_4$ | " | O | C=O | Racemic modification |
| 56 | 1-naphthyl group | 4,5,6,7-Cl$_4$ | " | O | C=O | S-form |
| 57 | 1-naphthyl group | 4,5,6,7-Cl$_4$ | " | O | C=O | R-form |
| 58 | 1-naphthyl group | 4,5,6,7-F$_4$ | " | S | C=O | Racemic modification |
| 59 | 1-naphthyl group | 4,5,6,7-F$_4$ | " | S | C=O | S-form |
| 60 | 1-naphthyl group | 4,5,6,7-F$_4$ | " | S | C=O | R-form |
| 61 | 1-naphthyl group | 4,5,6,7-Cl$_4$ | " | S | C=O | Racemic modification |
| 62 | 1-naphthyl group | 4,5,6,7-Cl$_4$ | " | S | C=O | S-form |
| 63 | 1-naphthyl group | 4,5,6,7-Cl$_4$ | " | S | C=O | R-form |
| 64 | Cyclohexyl group | — | " | O | C=O | Racemic modification |
| 65 | Cyclohexyl group | — | " | O | C=O | S-form |
| 66 | Cyclohexyl group | — | " | O | C=O | R-form: |
| 67 | Cyclohexyl group | 4,5,6,7-F$_4$ | " | O | C=O | Racemic modification |
| 68 | Cyclohexyl group | 4,5,6,7-F$_4$ | " | O | C=O | S-form: 147~148 |
| 69 | Cyclohexyl group | 4,5,6,7-F$_4$ | " | O | C=O | R-form: 147~148 |
| 70 | Cyclohexyl group | — | " | S | C=O | Racemic modification |
| 71 | Cyclohexyl group | — | " | S | C=O | S-form: |
| 72 | Cyclohexyl group | — | " | S | C=O | R-form: |
| 73 | Cyclohexyl group | 4,5,6,7-F$_4$ | " | S | C=O | Racemic modification |
| 74 | Cyclohexyl group | 4,5,6,7-F$_4$ | " | S | C=O | S-form: |
| 75 | Cyclohexyl group | 4,5,6,7-F$_4$ | " | S | C=O | R-form: |
| 76 | Cyclohexyl group | 4,5,6,7-Cl$_4$ | " | S | C=O | Racemic modification |

TABLE 1-continued (I')

| Comp. No. | R' | (X)$_m$ | Z' | Y | Q$_3$ | Physical properties (mp: °C.) |
|---|---|---|---|---|---|---|
| 77 | Cyclohexyl group | 4,5,6,7-Cl$_4$ | " | S | C=O | S-form: |
| 78 | Cyclohexyl group | 4,5,6,7-Cl$_4$ | " | S | C=O | R-form: |
| 79 | Phenyl group | 4-NH$_2$ | " | O | C=O | Racemic modification |
| 80 | Phenyl group | 4-NH$_2$ | " | O | C=O | S-form: |
| 81 | Phenyl group | 4-NH$_2$ | " | O | C=O | R-form: |
| 82 | Phenyl group | 4-NO$_2$ | " | O | C=O | Racemic modification |
| 83 | Phenyl group | 4-NO$_2$ | " | O | C=O | S-form: 115–117 |
| 84 | Phenyl group | 4-NO$_2$ | " | O | C=O | R-form: 115–117 |
| 85 | 4-nitrophenyl group | 4,5,6,7-F$_4$ | CH$_3$ | O | C=O | Racemic modification |
| 86 | 4-nitrophenyl group | " | " | O | C=O | S-form: 158–159.5 |
| 87 | 4-nitrophenyl group | " | " | O | C=O | R-form: 158–160 |
| 88 | 4-aminophenyl group | 4,5,6,7-F$_4$ | CH$_3$ | O | C=O | Racemic modification |
| 89 | 4-amimophenyl group | " | " | O | C=O | S-form: 175–177 |
| 90 | 4-amimophenyl group | " | " | O | C=O | R-form: 175–177 |
| 91 | 4-nPrCONH-phenyl group | 4,5,6,7-F$_4$ | CH$_3$ | O | C=O | Racemic modification |
| 92 | 4-nPrCONH-phenyl group | " | " | O | C=O | S-form: 174–175 |
| 93 | 4-nPrCONH-phenyl group | " | " | O | C=O | R-form: 174–175 |
| 94 | 4-methyl-phenyl group | 4,5,6,7-F$_4$ | CH$_3$ | O | C=O | Racemic modification |
| 95 | 4-methyl-phenyl group | " | " | O | C=O | S-form: 123–124 |
| 96 | 4-methyl-phenyl group | 4,5,6,7-F$_4$ | " | O | C=O | R-form: 123–124 |

Now, NMR data of the representative examples of the compounds of the present invention are listed in Table 2. The compound No. in Table 2 is the same as the compound No. in Table 1.

TABLE 2

| Compound No. | $^1$H-NMR δ ppm [solvent; CDCl$_3$] | Optical rotation [α]$^{20}_D$ |
|---|---|---|
| 17 | 500 MHz 1.91 (3 H, d, J = 7.32 Hz), 5.53 (1 H, q, J = 7.32 Hz), 7.29–7.37 (3 H, m), 7.48 (2 H, d, J = 7.32 Hz) | –42.2° (C = 0.386 AcOEt) |
| 18 | 500 MHz 1.92 (3 H, d, J = 7.32 Hz), 5.53 (1 H, q, J = 7.32 Hz), 7.29–7.36 (3 H, m), 7.48 (2 H, d, J = 7.32 Hz) | 41.5° (C = 0.348 AcOEt) |
| 49 | 400 MHz 2.01 (3 H, d, J = 6.84 Hz), 6.28 (1 H, q, J = 6.84 Hz), 7.46 (1 H, t, J = 6.84 Hz), 7.50–7.54 (2 H, m), 7.84 (2 H, t, J = 8.3O Hz), 7.97 (1 H, d, J = 7.32 Hz), 8.10 (1 H, t, J = 8.30 Hz) | –42.1° (C = 0.097 EtOH) |
| 50 | 400 MHz 2.02 (3 H, d, J = 6.84 Hz), 6.29 (1 H, q, J = 6.84 Hz), 7.47(1 H, t, J = 6.84 Hz), 7.51–7.55(2 H, m), 7.85 (2 H, t, J = 8.30 Hz), 7.98 (1 H, d, J = 7.32 Hz), 8.10 (1 H, t, J = 8.30 Hz) | 40.9° (C = 0.089 EtOH) |
| 68 | 500 MHz 0.86–1.00 (2 H, m), 1.10–1.28 (3 H, m), 1.44 (3 H, d, J = 6.84 Hz), 1.52–2.00 (5 H, m), 3.94–4.00 (1 H, m) | 5.26° (C = 0.618 AcOEt) |
| 69 | 400 MHz 0.86–1.00 (2 H, m), 1.10–1.28 (3 H, m), 1.44 (3 H, d, J = 6.84 Hz), 1.52–2.00 (5 H, m), 3.94–4.00(1 H, m) | –5.13° (C = 0.658 AcOEt) |
| 83 | 500 MHz 1.94 (3 H, d, J = 7.32 Hz), 5.59 (1 H, q, J = 7.32 Hz), 7.28–7.36(3 H, m), 7.51 (2 H, d, J = 7.81 Hz), 7.87 (1 H, t, J = 7.81 Hz), 8.06 (2 H, dd, J = 7.81 Hz, 2.93 Hz) | |
| 84 | 400 MHz 1.94 (3 H, d, J = 7.32 Hz), 5.59 (1 H, q, J = 7.32 Hz), 7.28–7.36 (3 H, m), 7.51 (2 H, d, J = 7.81 Hz), 7.87(1 H, t, J = 7.81 Hz), 8.06 (2 H, dd, J = 7.81 Hz, 2.93 Hz) | |

The results of elementary analysis of the compounds No.17–18, No.49–50 and No.68–69 are as follows.

Compound No. 17:

| Theoretical values | C; 59.45 | H; 2.81 | N; 4.33 |
| Observed values | C; 59.50 | H; 2.81 | N; 4.36 |

Compound No. 18:

| Theoretical values | C; 59.45 | H; 2.81 | N; 4.33 |
| Observed values | C; 59.41 | H; 2.88 | N; 4.45 |

Compound No. 49:

| Theoretical values | C; 64.35 | H; 2.97 | N; 3.75 |
| Observed values | C; 64.35 | H; 2.92 | N; 3.90 |

Compound No. 50:

| Theoretical values | C; 64.35 | H; 2.97 | N; 3.75 |
| Observed values | C; 64.35 | H; 2.92 | N; 3.82 |

Compound No. 68:

| Theoretical values | C; 58.36 | H; 4.59 | N; 4.25 |
| Observed values | C; 58.51 | H; 4.69 | N; 4.25 |

Compound No. 69:

| Theoretical values | C; 58.36 | H; 4.59 | N; 4.25 |
| Observed values | C; 58.32 | H; 4.40 | N; 4.35 |

Synthesis Example 9

Synthesis of N-(2,6-diisopropylphenyl)isoindoline (compound No.144 as Described Hereinafter)

0.5 g of o-phthalaldehyde and 0.661 g of 2,6-duisopropylaniline were dissolved in 20 ml of dichloromethane, 1 ml of acetic acid was added thereto, and the mixture was reacted at room temperature for 25 minutes.

After the reaction was finished, the reaction mixture was washed with sodium hydrogen carbonate aqueous solution, washed with water, washed with saturated aqueous sodium chloride, and dried over anhydrous magnesium sulfate, followed by filtration. The obtained filtrate was concentrated and dried and solidified. Then, it was recrystallized by using a mixture of hexane and dichloromethane, to obtain 0.792 g of the specified substance having a melting point of 130.9–132.0° C.

Synthesis Example 10

Synthesis of N-(2,6-diisopropylphenyl)-5-tert-butyl phthalimide (Compound No.173 as Described Hereinafter)

0.605 g of 4-tert-butylphthalic anhydride and 0.630 g of 2,6-diisopropylaniline were mixed, and the mixture was reacted at a temperature of 200° C. for 1 hour.

After the reaction was finished, the reaction mixture was dissolved in ethyl acetate, washed with sodium hydrogen carbonate aqueous solution, washed with water, and washed with saturated aqueous sodium chloride. Then, it was dried over anhydrous magnesium sulfate and subjected to filtration. The filtrate was concentrated and dried and solidified. Then, it was recrystallized by using a mixture of hexane and dichloromethane, to obtain 0.7055 g of the specified substance having a melting point of 234.0–234.8° C.

Synthesis Example 11

Synthesis of N-(2,6-diisopropylphenyl) thiophthalimide (Compound No.174 as Described Hereinafter)

(1) 7.41 g of phthalic anhydride and 8.86 g of 2,6-diisopropylaniline were mixed, and reacted at a temperature of 180° C. for 2 hours.

After the reaction was finished, the reaction mixture was dissolved in ethyl acetate, washed with sodium hydrogen carbonate aqueous solution, washed with water, and washed with saturated aqueous sodium chloride. Then, it was dried over anhydrous magnesium sulfate and subjected to filtration. The filtrate was concentrated and dried and solidified. Then, it was recrystallized by using a mixture of hexane and dichloromethane, to obtain 9.06 g (yield 62.5%) of N-(2,6-diisopropylphenyl)phthalimide having a melting point of 172.1° C.

(2) 0.3 g of N-(2,6-diisopropylphenyl)phthalimide was dissolved in 10 ml of xylene, 0.217 g of di-phosphorus pentasulfide (dimer) was added thereto, and the mixture was reacted under reflux for 1.5 hours.

After the reaction was finished, the reaction mixture was purified by silica gel column chromatography (eluent: ethyl acetate/hexane=1/15), to obtain 0.164 g of the specified substance having a melting point of 130.5–131.6° C. and 0.033 g of N-(2,6-diisopropylphenyl)dithiophthalimide.

Representative examples of the compounds of the present invention synthesized based on the Synthesis Examples or various methods for producing the compounds of the present invention as mentioned above are listed in Table 3.

TABLE 3

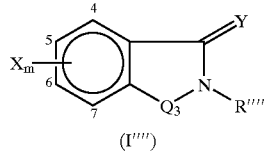

(I'''')

| Comp. | R'''' | $X_m$ | Y | $Q_3$ | Physical properties (mp.: ° C.) |
|---|---|---|---|---|---|
| 101 | Adamanthyl group | — (m = 0; the same applies hereinafter) | O | $CH_2$ | |
| 102 | Adamanthyl group | 4-F | O | $CH_2$ | |
| 103 | Adamanthyl group | 5-F | O | $CH_2$ | |
| 104 | Adamanthyl group | 4,7-$F_2$ | O | $CH_2$ | |
| 105 | Adamanthyl group | 4,7-$Cl_2$ | O | $CH_2$ | |
| 106 | Adamanthyl group | 5,6-$Cl_2$ | O | $CH_2$ | |
| 107 | Adamanthyl group | 4,5,6,7-$F_4$ | O | $CH_2$ | |
| 108 | Adamanthyl group | 4,5,6,7-$Cl_4$ | O | $CH_2$ | |
| 109 | Adamanthyl group | 5-$CH_3$ | O | $CH_2$ | |
| 110 | Adamanthyl group | 5-$CH(CH_3)_2$ | O | $CH_2$ | |
| 111 | Adamanthyl group | 5-$C(CH_3)_3$ | O | $CH_2$ | |
| 112 | Adamanthyl group | — | S | $CH_2$ | |
| 113 | Adamanthyl group | 4-F | S | $CH_2$ | |
| 114 | Adamanthyl group | 5-F | S | $CH_2$ | |
| 115 | Adamanthyl group | 4,7-$F_2$ | S | $CH_2$ | |
| 116 | Adamanthyl group | 4,7-$Cl_2$ | S | $CH_2$ | |
| 117 | Adamanthyl group | 5,6-$Cl_2$ | S | $CH_2$ | |
| 118 | Adamanthyl group | 4,5,6,7-$F_4$ | S | $CH_2$ | |
| 119 | Adamanthyl group | 4,5,6,7-$Cl_4$ | S | $CH_2$ | |
| 120 | Adamanthyl group | 5-$CH_3$ | S | $CH_2$ | |
| 121 | Adamanthyl group | 5-$CH(CH_3)_2$ | S | $CH_2$ | |
| 122 | Adamanthyl group | 5-$C(CH_3)_3$ | S | $CH_2$ | |
| 123 | Adamanthyl group | 4-F | O | C=O | |
| 124 | Adamanthyl group | 5-F | O | C=O | |
| 125 | Adamanthyl group | 4,7-$F_2$ | O | C=O | |
| 126 | Adamanthyl group | 4,7-$Cl_2$ | O | C=O | |
| 127 | Adamanthyl group | 5,6-$Cl_2$ | O | C=O | |
| 128 | Adamanthyl group | 4,5,6,7-$F_4$ | O | C=O | 175.2–175.9 |
| 129 | Adamanthyl group | 4,5,6,7-$Cl_4$ | O | C=O | |
| 130 | Adamanthyl group | 5-$CH_3$ | O | C=O | |
| 131 | Adamanthyl group | 5-$CH(CH_3)_2$ | O | C=O | |
| 132 | Adamanthyl group | 5-$C(CH_3)_3$ | O | C=O | |

TABLE 3-continued (Structure I'''')

| Comp. | R"" | $X_m$ | Y | $Q_3$ | Physical properties (mp.: °C.) |
|---|---|---|---|---|---|
| 133 | Adamanthyl group | — | S | C=O | |
| 134 | Adamanthyl group | 4-F | S | C=O | |
| 135 | Adamanthyl group | 5-F | S | C=O | |
| 136 | Adamanthyl group | 4,7-$F_2$ | S | C=O | |
| 137 | Adamanthyl group | 4,7-$Cl_2$ | S | C=O | |
| 138 | Adamanthyl group | 5,6-$Cl_2$ | S | C=O | |
| 139 | Adamanthyl group | 4,5,6,7-$F_4$ | S | C=O | |
| 140 | Adamanthyl group | 4,5,6,7-$Cl_4$ | S | C=O | |
| 141 | Adamanthyl group | 5-$CH_3$ | S | C=O | |
| 142 | Adamanthyl group | 5-$CH(CH_3)_2$ | S | C=O | |
| 143 | Adamanthyl group | 5-$C(CH_3)_3$ | S | C=O | |
| 144 | 2,6-diisopropyl phenyl group | — | O | $CH_2$ | 130.9–132.0 |
| 145 | 2,6-diisopropyl phenyl group | 4-F | O | $CH_2$ | |
| 146 | 2,6-diisopropyl phenyl group | 5-F | O | $CH_2$ | |
| 147 | 2,6-diisopropyl phenyl group | 4,7-$F_2$ | O | $CH_2$ | |
| 148 | 2,6-diisopropyl phenyl group | 4,7-$Cl_2$ | O | $CH_2$ | |
| 149 | 2,6-diisopropyl phenyl group | 5,6-$Cl_2$ | O | $CH_2$ | |
| 150 | 2,6-diisopropyl phenyl group | 4,5,6,7-$F_4$ | O | $CH_2$ | |
| 151 | 2,6-diisopropyl phenyl group | 4,5,6,7-$Cl_4$ | O | $CH_2$ | |
| 152 | 2,6-diisopropyl phenyl group | 5-$CH_3$ | O | $CH_2$ | |
| 153 | 2,6-diisopropyl phenyl group | 5-$CH(CH_3)_2$ | O | $CH_2$ | |
| 154 | 2,6-diisopropyl phenyl group | 5-$C(CH_3)_3$ | O | $CH_2$ | |
| 155 | 2,6-diisopropyl phenyl group | — | S | $CH_2$ | |
| 156 | 2,6-diisopropyl phenyl group | 4-F | S | $CH_2$ | |
| 157 | 2,6-diisopropyl phenyl group | 5-F | S | $CH_2$ | |
| 158 | 2,6-diisopropyl phenyl group | 4,7-$F_2$ | S | $CH_2$ | |
| 159 | 2,6-diisopropyl phenyl group | 4,7-$Cl_2$ | S | $CH_2$ | |
| 160 | 2,6-diisopropyl phenyl group | 5,6-$Cl_2$ | S | $CH_2$ | |
| 161 | 2,6-diisopropyl phenyl group | 4,5,6,7-$F_4$ | S | $CH_2$ | |
| 162 | 2,6-diisopropyl phenyl group | 4,5,6,7-$Cl_4$ | S | $CH_2$ | |
| 163 | 2,6-diisopropyl phenyl group | 5-$CH_3$ | S | $CH_2$ | |
| 164 | 2,6-diisopropyl phenyl group | 5-$CH(CH_3)_2$ | S | $CH_2$ | |
| 165 | 2,6-diisopropyl phenyl group | 5-$C(CH_3)_3$ | S | $CH_2$ | |
| 166 | 2,6-diisopropyl phenyl group | 4-F | O | C=O | 163.4–163.8 |
| 167 | 2,6-diisopropyl phenyl group | 5-F | O | C=O | 168.3–169.2 |
| 168 | 2,6-diisopropyl phenyl group | 4,7-$F_2$ | O | C=O | 164.9–165.2 |
| 169 | 2,6-diisopropyl phenyl group | 4,7-$Cl_2$ | O | C=O | |
| 170 | 2,6-diisopropyl phenyl group | 5,6-$Cl_2$ | O | C=O | 190.9–191.3 |
| 171 | 2,6-diisopropyl phenyl group | 5-$CH_3$ | O | C=O | 162.9–163.2 |
| 172 | 2,6-diisopropyl phenyl group | 5-$CH(CH_3)_2$ | O | C=O | |
| 173 | 2,6-diisopropyl phenyl group | 5-$C(CH_3)_3$ | O | C=O | 234.0–234.8 |
| 174 | 2,6-diisopropyl phenyl group | — | S | C=O | 130.5–131.6 |
| 175 | 2,6-diisopropyl phenyl group | 4-F | S | C=O | |
| 176 | 2,6-diisopropyl phenyl group | 5-F | S | C=O | |
| 177 | 2,6-diisopropyl phenyl group | 4,7-$F_2$ | S | C=O | |
| 178 | 2,6-diisopropyl phenyl group | 4,7-$Cl_2$ | S | C=O | |
| 179 | 2,6-diisopropyl phenyl group | 5,6-$Cl_2$ | S | C=O | |
| 180 | 2,6-diisopropyl phenyl group | 4,5,6,7-$F_2$ | S | C=O | 171.0–173.0 |
| 181 | 2,6-diisopropyl phenyl group | 4,5,6,7-$Cl_2$ | S | C=O | |
| 182 | 2,6-diisopropyl phenyl group | 5-$CH_3$ | S | C=O | |
| 183 | 2,6-diisopropyl phenyl group | 5-$CH(CH_3)_2$ | S | C=O | |
| 184 | 2,6-diisopropyl phenyl group | 5-$C(CH_3)_3$ | S | C=O | |
| 185 | 2,6-diisopropyl phenyl group | 4-OH | S | C=O | |
| 186 | 2,6-diisopropyl phenyl group | 5-OH | S | C=O | |
| 187 | 2,6-diisopropyl phenyl group | 4-$NH_2$ | S | C=O | |
| 188 | 2,6-diisopropyl phenyl group | 5-$NH_2$ | S | C=O | |
| 189 | 2,6-diisopropyl phenyl group | 4-$NO_2$ | S | C=O | |
| 190 | 2,6-diisopropyl phenyl group | 5-$NO_2$ | S | C=O | |
| 191 | 2,6-diisopropyl phenyl group | 4-CN | O | C=O | |
| 192 | 2,6-diisopropyl phenyl group | 4-$CF_3$ | O | C=O | |
| 193 | 2,6-diisopropyl phenyl group | 5-$O(CH_2)_5CH_3$ | O | C=O | 117–118 |
| 194 | 2-methylthio phenyl group | 4-OH | O | C=O | 152.5~154.0 |
| 195 | 2-methylthio phenyl group | 5-$CH_3$ | O | C=O | 175–177 |
| 196 | 2-methylthio phenyl group | 4-$NH_2$ | O | C=O | 148~150 |

NMR data of the representative examples of the compounds of the present invention are listed in Table 4. The compound No. in Table 4 is the same as the compound No. in Table 3.

TABLE 4

| Compound No. | $^1$H-NMR δ ppm [solvent; CDCl$_3$] | |
|---|---|---|
| 128 | 500 MHz | 1.71 (3 H, d, J = 12.3), 1.77 (3 H, dd, J = 12.3, 1.73), 2.17 (3 H, s), 2.46 (6 H, d, J = 1.73) |
| 144 | 500 MHz | 7.99 (1 H, d, J = 7.43), 7.63 (1 H, dt, J = 7.43, 1.12), 7.56 (1 H, t, J = 7.43), 7.53 (1 H, d, J = 7.43), 7.40 (1 H, t, J = 7.63), 7.26 (2 H, d, J = 7.63), 4.58 (2 H, s), 2.77 (2 H, 7 fission, J = 6.90), 1.21 (12 H, d, J = 6.90) |
| 166 | 500 MHz | 1.17 (6 H, d, J = 6.72), 1.18 (6 H, d, J = 6.72), 2.70 (2 H, quint, J = 6.72), 7.29 (2 H, d, J = 7.94), 7.50~7.44 (2 H, m), 7.84~7.78 (2 H, m) |
| 167 | 500 MHz | 1.17 (12 H, d, J = 6.83), 2.69 (2 H, quint, J = 6.83) 7.30 (2 H, d, J = 7.83), 7.47 (1 H, t, J = 7.83). 7.50 (1 H, dd, J = 8.54, 2.45), 7.64 (1 H, dd, J = 8.22, 2.45), 7.98 (1 H, dd, J = 8.22, 4.58) |
| 168 | 500 MHz | 1.18 (12 H, d, J = 6.77), 2.69 (2 H, quint, J = 6.77), 7.29 (2 H, d, J = 7.93), 7.47 (1 H, t, J = 7.93), 7.49 (2 H, d, J = 5.19) |
| 170 | 500 MHz | 1.16 (12 H, d, J = 6.83), 2.64 (2 H, quint, J = 6.83), 7.29 (2 H, d, J = 7.83), 7.47(1 H, t, J = 7.83), 8.06 (2 H, d, J = 0.6) |
| 171 | 60 MHz | 7.14 7.98 (6 H, m), 2.73 (2 H, 7 fission, J = 6.4), 2.57 (3 H, s), 1.20 (12 H, d, J = 6.4) |
| 173 | 500 MHz | 8.01 (1 H, d, J = 1.83), 7.90 (1 H, d, J = 7.79), 7.84 (1 H, dd, J = 7.79, 1.83), 7.46 (1 H, t, J =7.83), 7.30 (2 H, d, J = 7.83), 2.73 (2 H, 7 fission, J = 6.87), 1.43 (9 H, s), 1.17 (6 H, d, J = 6.87), 1.16 (6 H, d, J = 6.87) |
| 174 | 500 MHz | 1.13 (12 H, d, J = 7.02), 2.61 (2 H, quint, J = 7.02), 7.31 (2 H, d, J = 7.84), 7.49 (1 H, t, J = 7.84), 7.83~7.77 (2 H, m), 7.92~7.88 (1 H, m), 8.10~8.06 (1 H, m) |

The results of the instrumental analysis of the compound No.180 in Table 3 are as follows.

Mass: M/Z 395 (M$^+$),362 (M-33: M-S), 320 (M-75: M-4F)

| Elementary analysis: | | | |
|---|---|---|---|
| Theoretical values | C; 60.75, | H; 4.33, | N; 3.54 |
| Observed values | C; 60.50, | H; 4.73 | N; 3.38 |

Synthesis Example 12

Synthesis of N-phenylphthalimide (Compound No.201 as Described Hereinafter)

1.48 g of phthalic anhydride and 0.931 g of aniline were mixed under cooling with ice, and the mixture was reacted at a temperature of 180° C. for 2 hours.

After the reaction was finished, the reaction mixture was dissolved in ethyl acetate, washed with sodium hydrogen carbonate aqueous solution, washed with water, and washed with saturated aqueous sodium chloride. Then, it was dried over anhydrous magnesium sulfate and subjected to filtration. The filtrate was concentrated and dried and solidified. Then, it was recrystallized by using ethanol, to obtain 1.10 g of the desired compound.

It showed the following physical properties and analyzed values.

mp. 209~211° C.

$^1$H-NMR (500 MHz, CDCl$_3$): δ7.96(2H, m), 7.80(2H, m), 7.52(2H, m), 7.43(3H, m)

$C_{14}H_9NO_2$

| Elementary analysis | | | |
|---|---|---|---|
| Experimental values: | C 75.22 | H 4.16 | N 6.55 |
| Theoretical values: | C 75.33 | H 4.06 | N 6.27 |

Synthesis Example 13

Synthesis of N-(2.6-diisopropylphenyl)-phthalimide (Compound No.202 as Described Hereinafter)

7.41 g of phthalic anhydride and 8.86 g of 2,6-diisopropylaniline were mixed, and reacted at a temperature of 180° C. for 2 hours.

After the reaction was finished, the reaction mixture was dissolved in ethyl acetate, washed with sodium hydrogen carbonate aqueous solution, washed with water, and washed with saturated aqueous sodium chloride. Then, it was dried over anhydrous magnesium sulfate and subjected to filtration. The filtrate was concentrated and dried and solidified. Then, it was recrystallized by using ethanol, to obtain 9.06 g (yield 62.5%) of the specified compound.

It showed the following physical properties and analyzed values.

mp. 172° C.

$^1$H-NMR(60 MHz, CDCl$_3$): δ7.87(4H, m), 7.26(3H, m),2.72(2H, q, J=8.8 Hz), 1.21(12H, d, J=8.8 Hz)

$C_{20}H_{21}NO_2$

| Elementary analysis | | | |
|---|---|---|---|
| Experimental values: | C 78.17 | H 6.74 | N 4.57 |
| Theoretical values: | C 78.15 | H 6.89 | N 4.56 |

Synthesis Example 14

Synthesis of N-(2,6-diisopropylphenyl)-4,5,6,7-tetra-fluoro-phthalimide (Compound No.203 as Described Hereinafter)

0.2 g of 3,4,5,6-tetra-fluorophthalic anhydride and 0.161 g of 2,6-diisopropylaniline were mixed, and the mixture was melted and reacted at a temperature of 150° C. for 2 hours.

After the reaction was finished, the reaction mixture was dissolved in ethyl acetate, dried over anhydrous magnesium sulfate, and subjected to filtration. The filtrate was concentrated and dried and solidified. Then, it was recrystallized by using a mixture of hexane and dichloromethane, to obtain 0.198 g (yield 57%) of the specified compound.

It showed the following physical properties and analyzed values.

mp. 167.0° C.

$^1$H-NMR(500 MHz, CDCl$_3$): δ7.48(1H, t, J=7.73 Hz), 7.30(2H, d, J=7.73 Hz), 2.63(2H, 7 fission, J=6.90 Hz), 1.17(12H, d, J=6.90 Hz)

$C_{20}H_{17}F_4NO_2$

| Elementary analysis | | | | |
|---|---|---|---|---|
| Experimental values: | C 63.04 | H 4.42 | N 3.77 | F 20.02 |
| Theoretical values: | C 63.32 | H 4.52 | N 3.69 | F 20.03 |

Synthesis Example 15

Synthesis of N-(2,6-diisopropylphenyl)-4-nitrophthalimide (Compound No.204 as Described Hereinafter)

0.386 g of anhydride obtained by dehydrating 3-nitrophthalic acid at a temperature of about 220° C., and 0.354 g of 2,6-diisopropylaniline were mixed, and reacted at a temperature of 180° C. for 4 hours. After the reaction was finished, the reaction mixture was dissolved in ethyl acetate, dried over anhydrous magnesium sulfate and subjected to filtration. The filtrate was concentrated and dried and solidified. Then, it was recrystallized by using a mixture of hexane and ethyl acetate, to obtain 0.320 g (yield 45%) of the specified compound.

It showed the following physical properties and analyzed values.

mp. 157~158° C.

$^1$H-NMR(500 MHz, CDCl$_3$): δ8.23(1H, d, J=7.86 Hz), 8.21(1H, d, J=7.86 Hz), 8.01(1H, d, J=7.86 Hz), 7.48(1H, t, J=7.83 Hz), 7.30(2H, d, J=7.83 Hz), 2.66(2H, 7 fission, J=6.61 Hz), 1.19(6H, d, J=6.61 Hz), 1.18(6H, d, J=6.1 Hz)

$C_{20}H_{20}N_2O_4$

| Elementary analysis | | | |
|---|---|---|---|
| Experimental values: | C 68.32 | H 5.74 | N 8.07 |
| Theoretical values: | C 68.17 | H 5.72 | N 7.95 |

Synthesis Example 16

Synthesis of N-(2,6-diisopropylphenyl)-5-nitrophthalimide (Compound No.205 as Described Hereinafter)

0.386 g of anhydride obtained by dehydrating 4-nitrophthalic acid (including 20% of 3-nitrophthalic acid) at a temperature of about 190° C., and 0.354 g of 2,6-diisopropylaniline were mixed, and reacted at a temperature of 180° C. for 4 hours. After the reaction was finished, the reaction mixture was dissolved in ethyl acetate, dried over anhydrous magnesium sulfate and subjected to filtration. The filtrate was concentrated and dried and solidified. Then, it was recrystallized by using a mixture of hexane and ethanol, to obtain 0.352 g (yield 50%) of the specified compound.

It showed the following physical properties and analyzed values.

mp. 161~162° C.

$^1$H-NMR(500 MHz, CDCl$_3$): δ8.81(1H, d, J=2.14 Hz), 8.71(1H, dd, J=8.14, 2.04 Hz), 8.18(1H, d, J=8.14 Hz), 7.49(1H, t, J=7.73 Hz), 7.32(2H, d, J=7.73 Hz), 2.64(2H, 7 fission, J=6.90 Hz), 1.17(12H, d, J=6.90 Hz)

$C_{20}H_{20}N_2O_4$

| Elementary analysis | | | |
|---|---|---|---|
| Experimental values: | C 68.41 | H 5.71 | N 7.93 |
| Theoretical values: | C 68.17 | H 5.72 | N 7.95 |

Representative examples of the compounds of the present invention synthesized based on the Synthesis Examples or various methods for producing the compounds of the present invention as mentioned above are listed in 5 Table 5.

TABLE 5

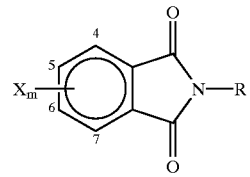

| Comp. No. | R | $X_m$ | Physical properties (mp.: ° C.) |
|---|---|---|---|
| 206 | 2-methylthio phenyl group | — | 162.8~163.0 |
| 207 | 2,6-dimethyl phenyl group | 4-OH | 145.8~146.8 |
| 208 | Phenyl group | 4-OH | 164.6~167.3 |
| 209 | 2,6-dimethyl phenyl group | 4,5,6,7-F$_4$ | 166.0~167.3 |
| 210 | 2,6-diisopropyl phenyl group | 4-NH$_2$ | 240.3~242.0 |
| 211 | 2,6-dimethyl phenyl group | 5-NH$_2$ | 194.0~194.2 |
| 212 | 2,6-diisopropyl phenyl group | 5-NH$_2$ | 252.8~254.1 |
| 213 | 2,6-diisopropyl phenyl group | 4-OH | 154.7~155.4 |
| 214 | 2,6-diisopropyl phenyl group | 5-OH | 199.6~201.0 |
| 215 | 2,6-dimethyl phenyl group | 5-OH | 200.4~201.4 |
| 216 | Phenyl group | 5-OH | 247.9~250.0 |

Synthesis Example 17

Synthesis of N-phenyl-homophthalimide (Compound No.A-1)

0.871 g (5.37 mmol) of homophthalic anhydride and 0.4 g (4.30 mmol) of aniline were mixed, and melted at a temperature of 200° C. for 1 hour. The reactant was dissolved in ethyl acetate, washed with aqueous NaHCO$_3$ solution, with water and then with saturated aqueous sodium chloride, dried over anhydrous MgSO$_4$, and subjected to filtration with a folded filter paper. The filtrate was concentrated and evaporated to dryness. The residue was recrystallized by using a mixture of CH$_2$Cl$_2$ and hexane, to obtain 0.565 g (yield 68%) of the specified substance as light yellow granulated crystals.

It showed the following physical properties and analyzed values.

mp. 186.7~187.9° C.

$^1$H-NMR(500 MHz, CDCl$_3$): δ8.25(1H, dd, J=7.63, 0.92), 7.65(1H, dt, J=7.63, 1.42), 7.43–7.54(4H, m), 7.35 (1H, d, J=7.32), 7.20–7.22(2H, m), 4.24(2H, s)

$C_{15}H_{11}NO_2$

| Elementary analysis | | | |
|---|---|---|---|
| Experimental values: | C 75.88 | H 4.63 | N 6.00 |
| Theoretical values: | C 75.94 | H 4.67 | N 5.90 |

Synthesis Example 18

Synthesis of N-(2,6-dimethylphenyl)-homophthalimide (Compound No.A-2)

0.67 g (4.13 mmol) of homophthalic anhydride and 0.4 g (3.30 mmol) of 2,6-dimethylaniline were mixed, and melted at a temperature of 200° C. for 1 hour. The reactant was dissolved in ethyl acetate, washed with aqueous NaHCO$_3$ solution, with water and then with saturated aqueous sodium chloride, dried over anhydrous MgSO$_4$, and subjected to filtration with a folded filter paper. The filtrate was concentrated and evaporated to dryness. The residue was recrystallized by using a mixture of CH$_2$Cl$_2$ and hexane, to obtain 0.565 g (yield 68%) of the specified substance as light yellow granulated crystals. It showed the following physical properties and analyzed values.

mp. 129.0~130.4° C.

$^1$H-NMR(500 MHz, CDCl$_3$): δ8.27(1H, d, J=7.54), 7.67 (1H, dt, J=7.54, 1.32), 7.49(1H, t, J=7.54), 7.38(1H, d, J=7.54), 7.25(1H, t, J=7.33), 7.18(2H, d, J=7.33), 4.25(2H, s),2.10(6H,s)

$C_{17}H_{15}NO_2$

| Elementary analysis | | | |
|---|---|---|---|
| Experimental values: | C 77.03 | H 5.68 | N 5.23 |
| Theoretical values: | C 76.96 | H 5.70 | N 5.28 |

Synthesis Example 19

Synthesis of N-(2.6-diisopropylphenyl)-homophthalimide (Compound No.A-3)

0.512 g (3.16 mmol) of homophthalic anhydride and 0.42 g (2.37 mmol) of 2,6-diisopropylaniline were mixed, and melted at a temperature of 200° C. for 1 hour. The reactant was dissolved in ethyl acetate, washed with aqueous NaHCO$_3$ solution, with water and then with saturated aqueous sodium chloride, dried over anhydrous MgSO$_4$, and subjected to filtration with a folded filter paper. The filtrate was concentrated and evaporated to dryness. The residue was recrystallized by using a mixture of CH$_2$Cl$_2$ and hexane, to obtain 0.351 g (yield 36%) of the specified substance as light purple leaflets. It showed the following physical properties and analyzed values.

mp. 184.2~185.9° C.

$^1$H-NMR(500 MHz, CDCl$_3$): δ8.27(1H, d, J=7.66), 7.67 (1H, dt, J=7.66, 1.32), 7.50(1H, t, J=7.66), 7.44(1H, t, J=7.83), 7.39(1H, d, J=7.66), 7.28(2H, d, J=7.83), 4.25(2H, s), 2.64(2H, 7 fission, J=6.87), 1.15(6H, d, J=6.87), 1.14(6H, d, J=6.87)

$C_{21}H_{23}NO_2$

| Elementary analysis | | | |
|---|---|---|---|
| Experimental values: | C 78.32 | H 7.14 | N 4.55 |
| Theoretical values: | C 78.47 | H 7.21 | N 4.36 |

Synthesis Example 20

Synthesis of N-phenyl-2,3-naphthalimide (Compound No.B-1)

0.91 g (4.59 mmol) of 2,3-naphthalic anhydride and 5 ml of aniline were mixed, and refluxed at a temperature of 190° C. for 1 hour. The reactant was dissolved in CHCl$_3$, washed with 1N-HCl (more than equivalent), with aqueous NaHCO$_3$ solution, then with water, and finally with saturated aqueous sodium chloride. Then it was dried over anhydrous MgSO$_4$, and subjected to filtration with a folded filter paper. The filtrate was concentrated and evaporated to dryness. The residue was recrystallized from CHCl$_3$, to obtain 0.36 g (yield 29%) of the specified substance as white needles. It showed the following physical properties and analyzed values.

mp. 274.2~274.8° C. p $^1$H-NMR(500 MHz, CDCl$_3$): δ8.47(2H,s), 8.08–8.13(2H, m), 7.72–7.76(2H, m),7.49–7.56(4H, m), 7.41–7.45(1H, m)

$C_{18}H_{11}NO_2$

| Elementary analysis | | | |
|---|---|---|---|
| Experimental values: | C 79.16 | H 4.13 | N 5.14 |
| Theoretical values: | C 79.11 | H 4.06 | N 5.13 |

Synthesis Example 21

Synthesis of N-(2,6-dimethylphenyl)2,3-naphthalimide (Compound No.B-2)

1.0 g (5.05 mmol) of 2,3-naphthalic anhydride and 5 ml of 2,6-dimethylaniline were mixed, followed by stirring at a temperature of 190° C. for 1 hour. The reaction product was dissolved in CHC13, and washed with 1N-HCl (more than equivalent), with aqueous NaHCO$_3$ solution, then with water, and finally with saturated aqueous sodium chloride. Then it was dried over anhydrous MgSO$_4$, and subjected to filtration with a folded filter paper. The filtrate was concentrated and evaporated to dryness. The residue was recrystallized by using a mixture of CH$_3$OH and hexane, to obtain 1.11 g (yield 73%) of the specified substance as white granulated crystals. It showed the following physical properties and analyzed values.

mp. 180.1~180.7° C.

$^1$H-NMR(500 MHz, CDCl$_3$): δ8.48(2H,s), 8.08–8.13(2H, m),7.72–7.76(2H, m),7.29(1H, t, J=7.53), 7.21(2H, d, J=7.53), 2.20(6H, s)

C$_{20}$H$_{15}$NO$_2$

| Elementary analysis | | | |
|---|---|---|---|
| Experimental values: | C 79.81 | H 5.11 | N 4.55 |
| Theoretical values: | C 79.72 | H 5.02 | N 4.65 |

Synthesis Example 22

Synthesis of N-(2,6-diisopropylphenyl) 2,3-naphthalimide (Compound No.B-3)

1.0 g (5.05 mmol) of 2,3-naphthalic anhydride and 5 ml of 2,6-diisopropylaniline were mixed, followed by stirring at a temperature of 190° C. for 1 hour. The reactant was dissolved in CHCl$_3$, washed with 1N-HCl (more than equivalent), with aqueous NaHCO$_3$ solution, then with water, and finally with saturated aqueous sodium chloride. Then it was dried over anhydrous MgSO$_4$, and subjected to filtration with a folded filter paper. The filtrate was concentrated and evaporated to dryness. The residue was recrystallized by using a mixture of CHCl$_3$ and C$_2$H$_5$OH, to obtain 0.611 g (yield 34%) of the specified substance as transparent granulated crystals. It showed the following physical properties and analyzed values.

mp. 251.0~252.3° C.

$^1$H-NMR(500 MHz, CDCl$_3$): δ8.49(2H, s),8.13–8.09(2H, m),7.76–7.72(2H, m), 7.48(1H, t, J=7.73), 7.32(2H, d, J=7.73), 2.77(2H, 7 fission, J=6.84), 1.18(12H, d, J=6.84)

C$_{24}$H$_{23}$NO$_2$

| Elementary analysis | | | |
|---|---|---|---|
| Experimental values: | C 80.72 | H 6.40 | N 3.86 |
| Theoretical values: | C 80.64 | H 6.49 | N 3.92 |

Synthesis Example 23

N-(2,6-diethylphenyl)-homophthalimide (Compound No.A-14)

162 mg (1.0 mmol) of homophthalic anhydride and 149 mg (1.0 mmol) of 2,6-diethylaniline were charged in an egg-plant type flask of 50 ml, followed by stirring under heating at a temperature of 180° C. for 2 hours. After cooled, the reactant was dissolved in chloroform, purified by silica gel column chromatography (eluent; ethylene chloride:methanol=30:1 v/v), and recrystallized from a mixed solvent of n-hexane-ethyl acetate, to obtain 220 mg of the specified substance as a light yellow powder.

Yield 75%; mp 108~110° C.; MS(EI+)m/z:293(M)$^+$;

$^1$H-NMR(500 MHz, CDCl$_3$) δ: 1.14(6H, t, J=7.33 Hz), 2.40(4H, q, J=7.33 Hz), 4.25(2H, s), 7.24(2H, d, J=7.83 Hz), 7.36–7.40(2H, m), 7.50(1H, t, J=7.83 Hz), 7.67(1H, dt, J=7.83, 1.47 Hz),8.26(1H, d, J=6.85 Hz);

Anal calcd for C$_{19}$H$_{19}$NO$_2$(293.37): C, 77.79; H, 6.53; N, 4.77.

Found: C, 77.69; H, 6.43; N, 4.56.

N-(2-methylthiophenyl)-phthalimide (Compound No.A-15) was synthesized in the same manner as in synthesis method of compound No.A-14.

Yield 81%; mp 106~108° C. (n-Hexane-Ethyl acetate); MS(EI+)m/z:283 (M)$^+$; $^1$H-NMR(500 MHz, CDCl$_3$) δ: 2.41 (3H, s), 4.20(1H, d, J=2.5 Hz), 4.3 0(1H, d, J=2.5 Hz), 7.17(1H, d, J=7.83 Hz), 7.31(1H, dt, J=7.83, 2.0 Hz), 7.34(1H, d, J=7.34 Hz), 7.40–7.47(1H, m), 7.48(1H, t, J=7.83 Hz), 7.65(1H, dt, J=7.83, 1.47 Hz), 8.26(1H, dd, J=7.83,1.47 Hz);

Anal calcd for C$_{16}$H$_{13}$NO$_2$S: C, 67.82; H, 4.62; N, 4.94.

Found: C, 67.86; H, 4.58; N, 4.70.

Specific examples of N-phenylimide compounds of the present invention are illustrated in Table 6 or Table 7.

TABLE 6

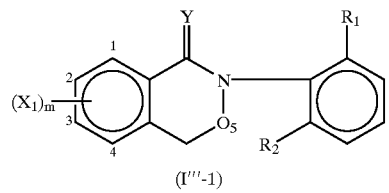

(I'''-1)

| Compound No. | R$_1$ | R$_2$ | X$_1$ | Y | m | Q$_5$ | Physical properties (° C.) |
|---|---|---|---|---|---|---|---|
| A-1 | H | H | — | O | 0 | C=O | m.p 186.7~187.9 |
| A-2 | —CH$_3$ | —CH$_3$ | — | O | 0 | C=O | m.p 129.0~130.4 |
| A-3 | —CH(CH$_3$)$_2$ | —CH(CH$_3$)$_2$ | — | O | 0 | C=O | m.p 184.2~185.9 |
| A-4 | —CH$_3$ | —CH(CH$_3$)$_2$ | — | O | 0 | C=O | — |
| A-5 | —CH(CH$_3$)$_2$ | —CH(CH$_3$)$_2$ | 1,2,3,4-F$_4$ | O | 4 | C=O | — |
| A-6 | —CH(CH$_3$)$_2$ | —CH(CH$_3$)$_2$ | — | O | 0 | CH$_2$ | — |
| A-7 | —CH(CH$_3$)$_2$ | —CH(CH$_3$)$_2$ | — | S | 0 | C=O | — |

TABLE 6-continued (I'''-1)

| Compound No. | $R_1$ | $R_2$ | $X_1$ | Y | m | $Q_5$ | Physical properties (° C.) |
|---|---|---|---|---|---|---|---|
| A-8 | —CH(CH$_3$)$_2$ | —CH(CH$_3$)$_2$ | 1,2,3,4-F$_4$ | S | 4 | C=O | — |
| A-9 | —CH(CH$_3$)$_2$ | —CH(CH$_3$)$_2$ | 1-NO$_2$ | O | 1 | C=O | — |
| A-10 | —CH(CH$_3$)$_2$ | —CH(CH$_3$)$_2$ | 1-NH$_2$ | O | 1 | C=O | — |
| A-11 | —CH(CH$_3$)$_2$ | —CH(CH$_3$)$_2$ | 1-CN | O | 1 | C=O | — |
| A-12 | —CH(CH$_3$)$_2$ | —CH(CH$_3$)$_2$ | 1-CF$_3$ | O | 1 | C=O | — |
| A-13 | —CH(CH$_3$)$_2$ | —CH(CH$_3$)$_2$ | 1-OH | O | 1 | C=O | — |
| A-14 | —CH$_2$CH$_3$ | —CH$_2$CH$_3$ | — | O | 0 | C=O | m.p 108~110 |
| A-15 | —SCH$_3$ | H | — | O | 0 | C=O | m.p 106~108 |
| A-16 | —CH(CH$_3$)$_2$ | H | — | O | 0 | C=O | m.p 158~160 |

TABLE 7

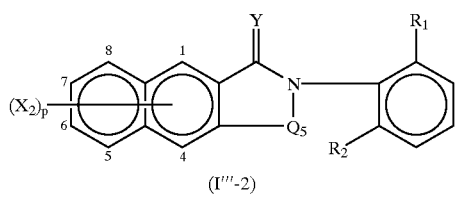

(I'''-2)

| Compound No. | $R_1$ | $R_2$ | $X_2$ | Y | p | $Q_5$ | Physical properties (° C.) |
|---|---|---|---|---|---|---|---|
| B-1 | H | H | — | O | 0 | C=O | m.p 274.2~274.8 |
| B-2 | —CH$_3$ | —CH$_3$ | — | O | 0 | C=O | m.p 180.1~180.7 |
| B-3 | —CH(CH$_3$)$_2$ | —CH(CH$_3$)$_2$ | — | O | 0 | C=O | m.p 251.0~252.3 |
| B-4 | —CH(CH$_3$)$_2$ | —CH(CH$_3$)$_2$ | 8-NO$_2$ | O | 1 | C=O | — |
| B-5 | —CH(CH$_3$)$_2$ | —CH(CH$_3$)$_2$ | 8-NH$_2$ | O | 1 | C=O | — |
| B-6 | —CH(CH$_3$)$_2$ | —CH(CH$_3$)$_2$ | 8-F | O | 1 | C=O | — |
| B-7 | —CH(CH$_3$)$_2$ | —CH(CH$_3$)$_2$ | 4,8-F$_2$ | O | 2 | C=O | — |
| B-8 | —CH$_3$ | —CH$_3$ | — | S | 0 | C=O | — |
| B-9 | —CH(CH$_3$)$_2$ | —CH(CH$_3$)$_2$ | — | S | 0 | C=O | — |
| B-10 | —CH(CH$_3$)$_2$ | —CH(CH$_3$)$_2$ | 8-NO$_2$ | S | 1 | C=O | — |

Now, Test Examples of the present invention will be described.

(Effect of Modulating TNF-α Production)

Human leukemia cells HL-60 produce tumor necrosis factor (TNF-α) by stimulation of Okadaic acid (9,10-Deepithio-9,10-didehydroacanthifolicin) or 12O-tetradecanoyl phorbol-13-acetate (TPA). Influences of the compounds of the present invention to production or secretion of TNF-α by them were observed.

Test Example 1
(Influences of the Compounds of the Present Invention to TNF-α Production or Secretion by Stimulation by Okadaic Acid)

Human leukemia cells (HL-60) were cultured by using a RPMI 1640 culture medium (including 5% fetal bovine serum), in a carbonic acid gas incubator (5% CO$_2$, humidified, 37° C.). Then, the cells were pre-cultured in a RPMI 1640 culture medium (including 10% fetal bovine serum). Okadaic acid was added thereto, so that the final concentration was 50 nM based on the HL-60 cells (5×10$^5$ cells/ml) in an exponentially growing stage. Then, the compound of the present invention was added thereto so that the predetermined concentration could be obtained, to prepare a cell suspension, which was then cultured in a carbonic acid gas incubator (5% CO$_2$, humidified, 37° C.). In this culture, a multiplate having 24 holes (produced by Corning) was used, and the cell suspension was injected in an amount of 0.5 ml per hole, to culture the cells.

16 hours after the culture started, the cells were removed by centrifugation (1000–2000 rpm×10 min), and the amount of TNF-α in the supernatant was measured in accordance with the method of Amersham, by using human TNF-α ELISA system (produced by Amersham).

The results are shown in Table 8. The values in the Table are values obtained by supposing the amount of TNF-α in the supernatant of the culture medium when treated only with Okadaic acid having a final concentration of 50 nM, 100%.

TABLE 8

Influences of the compounds of the present invention to production or secretion of TNF-α by Okadaic acid stimulation

| Compound No. | Treatment concentration | | | |
|---|---|---|---|---|
| | 1 nM | 10 nM | 100 nM | 0.3 μM |
| 17 | 100% | 99% | 95% | 70% |
| 18 | 97% | 55% | 8% | 2% |
| 49 | 100% | 102% | 100% | 101% |
| 50 | 100% | 88% | 43% | 2% |
| 68 | 102% | 101% | 96% | 65% |
| 69 | 101% | 95% | 59% | 10% |
| 83 | 100% | 99% | 85% | 61% |
| 84 | 99% | 104% | 88% | 52% |

Test Example 2
(Influences of the Compounds of the Present Invention to Production or Secretion of TNF-α by TPA Stimulation)

The same operation was carried out as in Test Example 1, except that TPA (produced by Sigma) having a final concentration of 10 nM was used, instead of Okadaic acid having a final concentration of 50 nM.

The measured results are shown in Table 9. The values in the Table are values obtained by supposing the amount of TNF-α in the supernatant of the culture medium when treated only with TPA having a final concentration of 10 nM, 100%.

TABLE 9

Influences of the compounds of the present invention to production or secretion of TNF-α by TPA stimulation

| Compound No. | Treatment concentration | | |
|---|---|---|---|
| | 10 nM | 100 nM | 0.3 μM |
| 17 | 102% | 120% | 143% |
| 18 | 100% | 101% | 97% |
| 49 | 100% | 99% | 101% |
| 50 | 100% | 100% | 100% |
| 68 | 103% | 115% | 124% |
| 69 | 100% | 102% | 98% |
| 83 | 122% | 187% | 239% |
| 84 | 100% | 121% | 195% |

Test Example 3

Human leukemia cells (HL-60) produce tumor necrosis factor (TNF-α) by stimulation of 12O-tetradecanoyl phorbol-13-acetate (TPA). The influences of the compounds of the present invention to production of TNF-α by it were observed.
(Enhancement of TNF-α Production or Secretion)

Human leukemia cells (HL-60) were cultured by using a RPMI 1640 culture medium (including 5% fetal bovine serum), in a carbonic acid gas incubator (5% $CO_2$, humidified, 37° C.). Then, the cells were pre-cultured in a RPMI 1640 culture medium (including 10% fetal bovine serum). TPA was added thereto, so that the final concentration was 10 nM based on the HL-60 cells ($5 \times 10^5$ cells/ml) in an exponentially growing stage. Then, the compound of the present invention was added thereto so that the predetermined concentration could be obtained, to prepare a cell suspension, which was then cultured in a carbonic gas incubator (5% $CO_2$, humidified, 37° C.). In this culture, a multiplate having 24 holes (produced by Corning) was used, and the cell suspension was injected in an amount of 0.5 ml per hole, to culture the cells.

16 hours after the culture started, the cells were removed by centrifugation (1000–2000 rpm×10 min), and the amount of TNF-α in the supernatant was measured in accordance with the method of Amersham, by using human TNF-α ELISA system (produced by Amersham).

The measured results are shown below. The values are obtained by supposing the amount of TNF-α when treated only with TPA having a final concentration of 10 nM, 100%.

| Compound No. | Treatment concentration (μM) | Amount of TNF (%) |
|---|---|---|
| A-3 | 10 | 258 |
| B-3 | 10 | 134 |

Test Example 4
(Inhibitory Effect to Aminopeptidase N)

Activity of aminopeptidase N can be measured by using, as a substrate, L-alanine-7-amido-4-methylcoumarin trifluoroacetate salt, and measuring fluorescence intensity of pigments produced after the reaction (European Journal Immunology, vol. 22, 923–930, 1992). Namely, as a substrate, L-alanine-7-amido-4-methylcoumarin trifluoroacetate salt (produced by Sigma, No. A4302) was added to $5 \times 10^4$ of acute lymphoblastic leukemia cells (MOLT-4) so that the final concentration was 0.2 mM, and reacted with a diluted solution (substrate buffer solution) prepared to have a predetermined concentration of the compound of the present invention at a temperature of 37° C. for 1 hour. As a control fraction, only buffer solution which did not contain the compound of the present invention was added. As the substrate buffer solution, 100 mM Hepes buffer solution pH 7.6 (including 120 mM sodium chloride, 5 mM potassium chloride, 1.2 mM magnesium sulfate and 0.5% bovine serum albumin) was used. After the reaction was finished, fluorescence intensity was measured by using MTP-32 Colonna microplate reader (produced by Colonna Electric) under measurement condition at an excitation wavelength of 380 nm and at an emission wavelength of 440 nm. The results are illustrated below. The values in the Table are based on fluorescence intensity of the control fraction, and represent the enzyme-inhibitory activity as $IC_{50}$ (μg/ml). The compounds of the present invention inhibited aminopeptidase N.

| Aminopeptidase N inhibiting activity $IC_{50}$ value | |
|---|---|
| Compound No. | (μg/ml) |
| A-2 | 14.1 |
| A-3 | <1.0 |
| A-14 | 0.0025 |
| A-15 | 0.2 |
| A-16 | 27.8 |

Test Example 5

[Inhibitory Activity to Platelet Derived Endothelial Cell Growth Factor (thymidine phosphorylase)]

(1) 100 mmol/l of thymidine (produced by Wako Pure Chemical Industries, Ltd.), 500 mmol/l of $K_2HPO_4$ (produced by Nacalai Tesque) and 0.5 mol/l of 2-morpholinoethansulfonic acid.$H_2O$ (pH 5.6; produced by Dojindo Laboratories) were prepared.

(2) The compound of the general formula (I) was dissolved in dimethylsulfoxide solution having a concentration of at most 10%, to prepare a test sample having a concentration of the compound of the general formula (I) of 1.0 mg/ml.

(3) 5 μg/ml of human platelet derived endothelial cell growth factor (produced by Sigma) was prepared.

(4) Into a tube having 20 μl of 100 mmol/l of thymidine, 20 μl of 500 mmol/l of $K_2HPO_4$, 100 μl of 0.5 mol/l of 2-morpholinoethansulfonic acid.$H_2O$ (pH 5.6) and 20 μl of the test sample having a concentration of the compound of the general formula (I) of 1.0 mg/ml, sterile water (autoclave-sterilized Milli Q water) and 20 μl of human platelet derived endothelial cell growth factor having a concentration of 5 μg/ml were added, so that the total amount was 200 μl and the final concentration of the compound of the general formula (I) was 100 μg/ml. The mixture was reacted at a temperature of 37° C. for 90 minutes.

(5) 50 μl of 2N-NaOH was added to 50 μl of the solution after the reaction, to prepare a solution for measurement.

(6) Absorbance of the solution for measurement was measured by using a spectrophotometer (SPECTRA max 250: produced by Molecular Devices) at a wavelength of 300 nm.

(7) Sterile water was added to 100 μl of buffer solution having 0.5 mol/l of 2-morpholinoethansulfonic acid.$H_2O$ (pH 5.6) and 20 μl of the test sample having a concentration of the compound of the general formula (I) of 1.0 mg/ml, so that the total amount was 200 μl, to prepare a solution of the compound of the general formula (I) having a final concentration of 100 μg/ml. Absorbance of a liquid having 50 μl of 2N-NaOH added to 50 μl of the solution, as a sample for measuring background, was measured at a wavelength of 300 nm. The measured value of absorbance ($OD_{sample}$) was obtained from the difference between absorbance measured in (6) and absorbance of the test sample for measuring background.

(8) The same operations from (1) to (7) were carried out, without adding test sample, and absorbance thus obtained was taken as the measured value of absorbance of control ($OD_{control}$).

(9) The inhibition ratio of platelet derived endothelial cell growth factor activity (thymidine phosphorylase activity) by the test sample having a concentration of the compound of the general formula (I) of 100 μg/ml was obtained by the formula:

Inhibition ratio=$(1-OD_{sample}/OD_{control}) \times 100(\%)$.

(10) With regard to test samples having a concentration of the compound of the general formula (I) of 0.1 μg/ml, 1 μg/ml and 10 μg/ml, the same operations from (4) to (9) were carried out, and the inhibition ratio of platelet derived endothelial cell growth factor activity (thymidine phosphorylase activity) was measured.

(11) 50% inhibition concentration of the test samples of the compound of the general formula (I) to activity of platelet derived endothelial cell growth factor (thymidine phosphorylase) was obtained from the results of (9) and (10), and taken as 50% inhibition concentration ($IC_{50}$) of the compound of the general formula (I) to activity of platelet derived endothelial cell growth factor (thymidine phosphorylase).

| Compound No. | $IC_{50}$ (μg/ml) |
|---|---|
| A-1 | 38 |
| A-2 | 61 |

Test Example 6

Influences of the compounds of the present invention to production or secretion of TNF-α by Okadaic acid stimulation were observed, in the same manner as in Test Example 1.

The measured results are shown in Table 10. As evident from Table 10, the compounds of the present invention suppressed production or secretion of TNF-α by HL-60 cells stimulated by Okadaic acid.

TABLE 10

Influences of the compounds of the present invention to production or secretion of TNF-α by Okadaic acid stimulation

| Compound No. | Treatment concentration | | |
|---|---|---|---|
| | 1 μM | 10 μM | 100 μM |
| 174 | 96% | 15% | 0% |
| | 10 nM | 100 nM | 1 μM |
| 180 | 70% | 35% | 0% |

Test Example 7

The influences of the compounds of the present invention to production or secretion of TNF-α by TPA stimulation were observed, in the same manner as in Test Example 2.

Measured results are shown in Table 11. As evident from Table 11, the compounds of the present invention enhanced production or secretion of TNF-α by HL-60 cells stimulated by TPA.

TABLE 11

Influences of the compounds of the present invention to production or secretion of TNF-α by TPA stimulation

| Compound No. | Treatment concentration | | | |
|---|---|---|---|---|
| | % | % | % | % |
| | 0.1 μM | 1 μM | 10 μM | 100 μM |
| 128 | 329 | 207 | — | — |
| 144 | — | — | — | 319 |
| 166 | — | 181 | 440 | — |
| 167 | — | 170 | 505 | — |
| 168 | — | 297 | 697 | — |
| 170 | — | 140 | — | — |
| 171 | — | — | 421 | — |

TABLE 11-continued

Influences of the compounds of the present invention to production or secretion of TNF-α by TPA stimulation

| Compound No. | Treatment concentration | | | |
|---|---|---|---|---|
| | % | % | % | % |
| 173 | — | — | 251 | – |
| 174 | — | 332 | 682 | 1326 |
| | 1 nM | 10 nM | 100 nM | 1 μM |
| 180 | 130 | 200 | 350 | — |

Test Example 8

(Influences of the Compounds of the Present Invention to Angiogenesis Under Skin of Mice)

By subcutaneously injecting a mixture having recombinant human fibroblast growth factor-basic added to matrigel, to the back of a mice, angiogenesis occurs under skin of the mice. By measuring the amount of hemoglobin in matrigel, angiogenesis can be quantified. Influences of the compounds of the present invention to angiogenesis were observed.

Matrigel (trademark; basement membrane matrix, phenol is not included, purchased from Becton Dickinson Labware) was added to Dulbecco's modified Eagle's medium (purchased from Sigma), so that the concentration was 9 mg/ml. Recombinant Human Fibroblast Growth Factor-basic (b-FGF, produced by Intergen) was added thereto, so that the concentration was 2 μg/700 μl. The mixture was subcutaneously injected to 6-week BALB/c male mice (Charles River Japan Inc.) in an amount of 700 μl per mouse. Everyday after matrigel injection, a suspension having the compound of the present invention added to 0.8% Tween 80 (purchased from Nacalai Tesque), so that the predetermined concentration could be obtained, was intraperitoneally injected to the mice. 8 days after matrigel injection, matrigel was taken out from the mice, which was then placed in 200 μl of 1% NH$_4$OH at room temperature for 4 hours, to extract hemoglobin. The extraction and matrigel together were subjected to centrifugal separation (10000 rpm, 5 min). 100 μl of the obtained supernatant and 500 μl of Drabkin's reagent (purchased from Sigma) were mixed and left at room temperature. After left more than 15 minutes, absorbance of the supernatant at a wavelength of 540 nm was measured by using a spectrophotometer SPECTRA max 250 (produced by Molecular Devices). The amount of hemoglobin in the supernatant was obtained from the standard curve prepared by using hemoglobin standard (purchased from Sigma), and the amount of hemoglobin per matrigel obtained from a mouse was calculated.

The results are shown in Table 12. The amount of the hemoglobin in each treatment fraction was corrected by the amount of hemoglobin wherein matrigel having no b-FGF added was injected to the mice, and 0.8% Tween 80 as a solvent alone was injected everyday. The compounds of the present invention inhibited angiogenesis occurred under skin of mice.

TABLE 12

Influences of the compounds of the present invention to angiogenesis under skin of mice

| Compound No. | Dose (mg/kg) | Amount of hemoglobin (μg/gel) |
|---|---|---|
| 174 | 0 | 307.3 (100) |
| | 100 | 164.8 (54) |

Test Example 9

Influences of the compounds of the present invention to aminopeptidase N activity were observed, in the same manner as in Test Example 4.

The measured results are shown in Table 13. As evident from Table 13, the compounds of the present invention inhibited aminopeptidase N. The values in Table are based on fluorescence intensity of the control fraction, and represent the enzyme-inhibitory activity as IC$_{50}$ (μg/ml)

TABLE 13

Influences of the compounds of the present invention to aminopeptidase N

| Compound No. | Aminopeptidase N inhibiting activity IC$_{50}$ (μg/ml) |
|---|---|
| 18 | 1.5 |
| 86 | 5.3 |
| 90 | 5 |
| 92 | 3.6 |
| 93 | 80 |
| 96 | 9.5 |
| 144 | 3.8 |
| 171 | 3.8 |
| 193 | 4.8 |
| 194 | 38 |
| 195 | 6.1 |
| 196 | 27.2 |
| 206 | 7.0 |
| 207 | 92.0 |
| 208 | 22.9 |
| 209 | 2.1 |
| 210 | 11.2 |
| 211 | 19.7 |
| 212 | 9.7 |
| 213 | 4.5 |
| 214 | 13.1 |
| 215 | 1.5 |
| 216 | 32.9 |

Test Example 10

Influences of the compounds of the present invention to production or secretion of TNF-α by Okadaic acid stimulation were observed, in the same manner as in Test Example 1.

The measured results are shown in Table 14. As evident from Table 14, the N-phenylphthalimide derivatives suppressed production or secretion of TNF-α by HL-60 cells stimulated by Okadaic acid.

TABLE 14

Influences of the compounds of the present
invention to production or secretion of TNF-α
by Okadaic acid stimulation

| Compound No. | Treatment concentration | | | | |
|---|---|---|---|---|---|
| | % | % | % | % | % |
| | 1 μM | 3 μM | 10 μM | 30 μM | 100 μM |
| 201 | 100 | 100 | 82 | 60 | 41 |
| 202 | 100 | 80 | 43 | 20 | 9 |
| | 1 nM | 3 nM | 10 nM | 30 nM | 100 nM |
| 203 | 100 | 93 | 75 | 42 | 0 |

Test Example 11

Influences of the compounds of the present invention to angiogenesis under skin of mice were observed, in the same manner as in Test Example 8.

The measured results are shown in Table 15. As evident from Table 15, the compounds of the present invention inhibited angiogenesis occurred under skin of mice.

TABLE 15

Influences of the compounds of the present
invention to angiogenesis under skin of mice

| Compound No. | Dose (mg/kg) | Amount of hemoglobin (μg/gel) |
|---|---|---|
| (a) Control | | 307.3 (100) |
| 202 | 10 | 235.4 (77) |
| | 100 | 152.5 (50) |
| 203 | 1 | 211.4 (69) |
| (b) Control | | 83.3 (100) |
| 17 | 1 | 17.3 (21) |
| | 5 | 25.7 (31) |
| 18 | 5 | 65.1 (78) |
| 50 | 5 | 65.4 (79) |
| 69 | 1 | 77.2 (93) |
| | 5 | 41.1 (49) |

Industrial Applicability

According to the present invention, the cyclic imide derivative or its salt makes it possible to modulate amount of TNF-α, inhibit angiogenesis and/or inhibit activity of aminopeptidase N in body, and thus it is useful to treat or prevent various diseases mentioned above.

What is claimed is:

1. An aminopeptidase N inhibitor composition which comprises a cyclic imide derivative represented by the general formula (I):

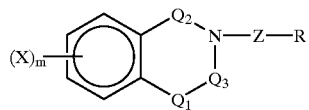

(I)

wherein $Q_1$ is —$CH_2$—, —O—, —S— or —NH—, each of $Q_2$ and $Q_3$ which are independent of each other, is —C(O)—, —C(S)— or —$CH_2$—, provided that at least one of $Q_2$ and $Q_3$ is —C(O)— or —C(S)—, Z is a single bond, R is an aryl group which may be substituted or a cycloalkyl group which may be substituted, X is a nitro group, an amino group which may be acylated, a cyano group, a trifluoromethyl group, a hydroxyl group, a halogen atom, an alkyl group, an alkoxy group or an alkylthio group, m is an integer of from 0 to 4, and when m is 2 or above, X may be the same or different, or its salt, and a pharmaceutically acceptable carrier.

2. The aminopeptidase N inhibitor composition according to claim 1, wherein in the cyclic imide derivative, $Q_1$ is —$CH_2$—.

3. The aminopeptidase N inhibitor composition according to claim 1, wherein in the cyclic imide derivative, $Q_1$ is —$CH_2$—, and R is a phenyl group which may be substituted.

4. An angiogenesis inhibitor composition which comprises a cyclic imide derivative represented by the general formula (I):

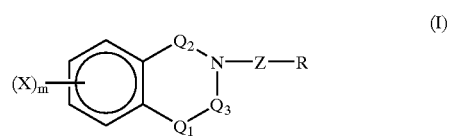

(I)

wherein $Q_1$ is —$CH_2$—, —O—, —S— or —NH—, each of $Q_2$ and $Q_3$ which are independent of each other, is —C(O)—, —C(S)—, or —$CH_2$—, provided that at least one of $Q_2$ and $Q_3$ is —C(O)— or —C(S)—, Z is a single bond, R is an aryl group which may be substituted or a cycloalkyl group which may be substituted, X is a nitro group, an amino group which may be acylated, a cyano group, a trifluoromethyl group, a hydroxyl group, a halogen atom, an alkyl group, an alkoxy group or an alkylthio group, m is an integer of from 0 to 4, when m is 2 or above, X may be the same or different, and provided that when Z is a single bond, R is an aryl group which may be substituted, or its salt, and a pharmaceutically acceptable carrier.

5. The angiogenesis inhibitor composition according to claim 4, wherein $Q_1$ in the cyclic imide derivative is —$CH_2$—.

6. The angiogenesis inhibitor composition according to claim 4, wherein in the cyclic imide derivative, $Q_1$ is —$CH_2$—, and R is a phenyl group which may be substituted, a naphthyl group which may be substituted or a cyclohexyl group which may be substituted.

7. The angiogenesis inhibitor composition according to claim 4, wherein in the cyclic imide derivative, $Q_1$ is —$CH_2$—, Z is a single bond, R is a phenyl group which may be substituted, a naphthyl group which may be substituted or a cyclohexyl group which may be substituted.

8. The angiogenesis inhibitor composition according to claim 4, wherein in the cyclic imide derivative, $Q_1$ is —$CH_2$—, Z is a single bond, R is a phenyl group which may be substituted, a naphthyl group which may be substituted or a cyclohexyl group which may be substituted, X is a fluorine atom and m is 4.

9. The aminopeptidase N inhibitor composition according to claim 1, which comprises an N-phenyl imide compound represented by the general formula (I'''-1):

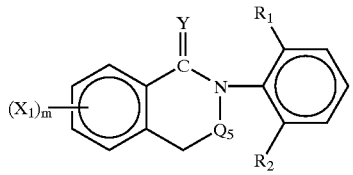

(I'''-1)

wherein each of $R_1$ and $R_2$ is a hydrogen atom, a lower alkyl group, a lower alkoxy group or a lower alkylthio group, Y is an oxygen atom or a sulfur atom, $X_1$ is a halogen atom, a nitro group, a cyano group, a trifluoromethyl group, a hydroxyl group, an amino group which may be acylated, an alkyl group, an alkoxy group or an alkylthio group, m is 0 or an integer of from 1 to 4, provided that when m is 2 or above, $X_1$ may be the same or different, and $Q_5$ is —C(O)— or —$CH_2$—, or its salt, and a pharmaceutically acceptable carrier.

10. The angiogenesis inhibitor composition according to claim 4, which comprises an N-phenylimide compound represented by the general formula (I'''−1):

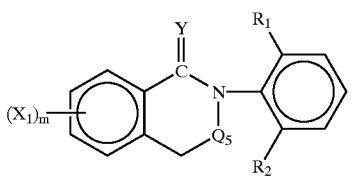

(I'''-1)

wherein each of $R_1$ and $R_2$ is a hydrogen atom, a lower alkyl group, a lower alkoxy group or a lower alkylthio group, Y is an oxygen atom or a sulfur atom, $X_1$ is a halogen atom, a nitro group, a cyano group, a trifluoromethyl group, a hydroxyl group, an amino group which may be acylated, an alkyl group, an alkoxy group or an alkylthio group, m is 0 or an integer of from 1 to 4, when m is 2 or above, X may be the same or different, and $Q_5$ is —C(O)— or —$CH_2$—, or its salt, and a pharmaceutically acceptable carrier.

* * * * *